(12) United States Patent
Uber, III et al.

(10) Patent No.: US 8,521,716 B2
(45) Date of Patent: *Aug. 27, 2013

(54) INTERFACE DEVICES AND METHODS FOR COLLECTION OF INFORMATION RELATED TO PROCEDURES

(75) Inventors: Arthur E. Uber, III, Pittsburgh, PA (US); John P. Friel, Pittsburgh, PA (US); David M. Griffiths, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/180,175

(22) Filed: Jul. 11, 2011

(65) Prior Publication Data

US 2011/0270633 A1    Nov. 3, 2011

Related U.S. Application Data

(60) Division of application No. 12/254,318, filed on Oct. 20, 2008, now Pat. No. 7,996,381, which is a continuation of application No. 10/143,562, filed on May 10, 2002, now Pat. No. 7,457,804.

(51) Int. Cl.
*G06F 17/30* (2006.01)

(52) U.S. Cl.
USPC ........... 707/708; 707/688; 707/721; 707/732; 707/751

(58) Field of Classification Search
USPC ................. 707/634, 688, 721, 732, 751, 708; 702/183; 705/2, 3; 600/428; 606/41, 34; 128/204.18

See application file for complete search history.

(56) References Cited

U.S. PATENT DOCUMENTS

| | | | |
|---|---|---|---|
| 3,839,708 | A | 10/1974 | Bredesen et al. |
| 5,377,258 | A | 12/1994 | Bro |
| 5,400,792 | A | 3/1995 | Hoebel et al. |
| 5,832,450 | A | 11/1998 | Myers et al. |
| 5,920,054 | A | 7/1999 | Uber, III |

(Continued)

FOREIGN PATENT DOCUMENTS

WO    0080522    10/2000

OTHER PUBLICATIONS

Philippe Pucheral et al., "Pico DBMS: Scaling down database techniques for the smartcard", ACM, 2001, pp. 120-132.

(Continued)

*Primary Examiner* — Thuy Pardo
(74) *Attorney, Agent, or Firm* — James Stevenson; Gregory L. Bradley; Jeffrey Karceski

(57) ABSTRACT

An interface device is used to collect information relating to procedures. The interface device is enabled to communicate with a first device, a second device and an information system. The interface device may be configured to receive before, during and/or after performance of each procedure, a set of personal identification information from the first device, the second device and/or the information system, and automatically, during and/or after performance of each procedure, a first set of procedure information from the first device and a second set of procedure information from the second device. The set of patient identification information is matched automatically with the first and second sets of procedure information related thereto for each procedure performed. A database automatically stores, as a record therein, the set of patient identification information and the first and the second sets of procedure information related thereto for each of the procedures performed.

43 Claims, 13 Drawing Sheets

(56) References Cited

U.S. PATENT DOCUMENTS

| | | |
|---|---|---|
| 6,249,705 B1 | 6/2001 | Snell |
| 6,681,003 B2 | 1/2004 | Linder et al. |
| 7,285,117 B2 * | 10/2007 | Krueger et al. ............ 606/34 |
| 7,574,368 B2 | 8/2009 | Pawlikowski et al. |
| 7,979,290 B2 * | 7/2011 | Dang ............................ 705/3 |
| 8,326,647 B2 * | 12/2012 | Chishti et al. ............... 705/2 |
| 2001/0020240 A1 | 9/2001 | Classen |
| 2002/0103622 A1 * | 8/2002 | Burge ........................ 702/183 |
| 2003/0009354 A1 | 1/2003 | Arbogast et al. |
| 2003/0055685 A1 | 3/2003 | Cobb et al. |
| 2003/0110059 A1 * | 6/2003 | Janas et al. .................. 705/2 |
| 2003/0145854 A1 * | 8/2003 | Hickle ................... 128/204.18 |
| 2004/0024311 A1 * | 2/2004 | Quaid, III ................. 600/428 |
| 2008/0215046 A1 * | 9/2008 | Messing et al. ............ 606/41 |
| 2009/0292556 A1 * | 11/2009 | Chishti et al. ............... 705/2 |
| 2010/0145730 A1 | 6/2010 | Abreu |

OTHER PUBLICATIONS

Todd Malan et al., "Handheld computer operating system program for collection of resident experience data", Obstetrics & Gynecology, 2000, pp. 1.

Kennelly, Robert J. "Improving Acute Care Through use of Medical Device Data", International Journal of Medical Informatics, 48, p. 145-149 (1998).

"Communication Standards in the Clinical Setting: An Introduction" HP Technology White Paper, Apr. 15, 1999.

Kennelly, Robert J., "Real Time Informatics", Health Systems Review, vol. 30, Issue 2, p. 54, Mar./Apr. 1997.

* cited by examiner

INTERFACE DEVICES AND METHODS FOR COLLECTION OF INFORMATION RELATED TO PROCEDURES

CROSS-REFERENCE TO RELATED APPLICATIONS

This application is a divisional of U.S. application Ser. No. 12/254,318 filed Oct. 20, 2008 now U.S. Pat. No. 7,996,381, which is a continuation of U.S. application Ser. No. 10/143,562, filed on May 10, 2002, now U.S. Pat. No. 7,457,804, the contents of which are incorporated herein by reference.

BACKGROUND OF THE INVENTION

A person's natural tendency is to perform a known task in the same manner in which he has performed the task numerous times in the past.

Similarly, when performing a particular task, a person's natural tendency is to rely on the same equipment that he has used successfully in the past.

Additionally, where standards have been established for the completion of a particular task, a person's natural tendency is to follow the accepted standards.

In the medical profession, these three tendencies are particularly pronounced. Naturally, where a person's health and life are at stake, it is entirely justified for those in the medical profession to take a conservative approach to medical treatment by relying on trusted techniques, equipment, and standards.

While conservatism fosters the perpetuation of sound and trusted medical procedures, the continued use of reliable equipment, and the practice of accepted standards, it also fosters a certain degree of stagnation. Those in the medical profession are less likely to embrace new and untested medical techniques, equipment, and standards before they have been proven to be safe and effective. In fact, those in the medical profession are likely to follow accepted medical practices, use accepted equipment, and rely on accepted standards even though technology may have advanced sufficiently to render them obsolete or, at a minimum, cast doubt on their current efficacy or applicability.

All of this means that new medical techniques, technologies, and standards, even those that may be more cost effective and beneficial than tried and tested techniques, technologies, and standards, are slow to be adopted. This slows the progress of medicine.

Presently, in order to assess the efficacy of a change in a medical technique, technology, or standard, a physician must perform the procedure, use the technology, or test the new standard with a number of patients in a number of multi-site clinical trials. Naturally, those trials must include a control group for proper assessment of the medical technique, technology, or standard.

Following clinical trials, the physician typically describes and publishes his findings in a suitable medical journal. In addition, he may present his findings to his peers at medical conferences. As can be readily understood, this process often may take a number of years. Moreover, the sheer magnitude of the undertaking often means that only the most deserving of medical techniques and technologies and the establishment of the most beneficial standards are pursued.

In addition, the enormous costs associated with studies prohibit most doctors and physicians from testing any techniques or equipment or from establishing new standards without assistance from large companies and research organizations that have sufficient financial resources to fund these activities.

For example, when performing a diagnostic evaluation that involves the use of a medical injector in combination with a scanning device (such as a CT (Computed Tomography) or MRI (Magnetic Resonance Imaging) scanner), it may be the widely accepted practice to inject contrast media into the patient at a rate of X ml per minute to assure that the diagnostic evaluation provides useable information to the physician. The standard rate of injection probably was established through the clinical trial method described above.

It may be the case, however, that the rate of injection of contrast media may not need to be as high as the rate recommended due to advances in scanning technology. For example, the sensitivity of the scanner used for a particular diagnostic may have improved (and probably has improved) since the development of the standard(s) associated with its use. Some doctors will adapt their protocols to the capabilities of the new equipment. These are often called "rapid adopters." However, other practitioners, despite advances in technology, may continue to use the established contrast flow rate simply because the flow rate falls within the standard established for the particular diagnostic technique.

The result of applying the established standard irrespective of any advances in medical equipment has several consequences. First, if the scanner's sensitivity has increased so that the standard flow rate is no longer required, the patient receives more contrast media than is required for the medical diagnostic. Not only does this increase the cost of the procedure (because more contrast media is used than is required), it also increases the possibility that the patient may have an adverse reaction to the contrast media. In addition, and perhaps more importantly, due to its increased sensitivity, the scanner's performance may be hindered by the use of contrast media at the standard rate if it performs optimally at a lower injection rate that is not recognized by the standard.

The same reluctance may be exhibited when new equipment is brought to the medical arena. For example, if an improved scanner is offered for use, rapid adopters will purchase and use the equipment to the benefit of their patients. Other doctors or practitioners may resist purchasing and using the equipment until its safety and efficacy are proven. As a result, patients may not benefit from the advances that the equipment offers to provide a more accurate diagnosis. Because of the cost and difficulty in proving the benefits of the improvement, as mentioned above, there often is significant delay in making this improvement available to all patients.

In summary, what the prior art and current practice fails to provide is a system or methodology for the appropriately rapid adoption of step-wise, incremental advances in medicine that develop on a continuing basis, the kind of incremental changes that result from daily practice. Simply, there are few, if any, existing mechanisms by which incremental advances may be shared with other practitioners in the medical profession to more rapidly advance medical care and quality, among other things.

The divergence between the conservative approach to the advance of medicine and the need for the reevaluation of standards and the evaluation of new medical techniques and equipment has created a technology gap in modern medicine that cries out for a solution.

At the same time, technological advances relating to information communication have been exploding. Home utility meters can automatically transmit readings for billing purposes. Copiers and other equipment can call a central office when their self-test software detects a failure or imminent failure. And, for some equipment, it is possible to remotely conduct equipment diagnosis and change equipment settings or software.

SUMMARY OF THE INVENTION

It is therefore an object of the present invention to provide a system that collects and disseminates information to facilitate the derivation and establishment of medical standards and best medical practices.

It is still another object of the present invention to provide a system and method that closes the gap that exists in modern medicine between methods and technologies that are being used and improvements to those methods and technologies that are being developed and introduced.

To accomplish this, the system of the present invention provides a centralized management of information about the medical equipment, procedures performed with that equipment, and the results of those procedures. The centralized database establishes a repository of information that can be relied upon to facilitate step-wise advancements in medical techniques, technologies, and standards.

In one aspect, the present invention also concerns a method for accumulating information about medical equipment and procedures with a particular sensitivity to reducing the cost associated with the manufacture and use of such equipment.

In another aspect, the present invention permits the centralized accumulation of information so that medical standards may be re-evaluated and adjusted continually.

In accordance with these objectives, the present invention offers a method and apparatus that fosters the collection and dissemination of information about newly-developed medical techniques, technologies, equipment, and standards so that new and improved techniques, technologies, equipment, and standards can be more rapidly brought to patients who may benefit from them, when appropriate.

One aspect of the invention is to provide an automated "benchmarking" procedure for the collection of information about the efficacy of medical devices, techniques, and standards that proliferate in the medical arena.

Among other things, "benchmarking" is now recognized as a powerful tool for improving the quality of products or services while reducing the costs associated with the use and manufacture of those products and the development of those services. As the word is now understood, "benchmarking" is a procedure, the basis of which involves the collection and assessment of sufficient volumes of information so that trends and outliers in that information may be identified and analyzed. Benchmarking may be used to learn how others accomplish similar tasks, what defects appear in products on a per million basis (or less), how satisfied doctors and physicians are with particular products, trends in employee turnover, and the efficacy of daily practices, depending upon the topic or field to which it is applied.

Successful benchmarking requires the successful collection and organization of the information that forms the basis of the analysis. As such, a benchmarking procedure that relies on individuals to manually collect information is less likely to succeed than a benchmarking procedure where the information is gathered and collected in an automated fashion. In other words, if data collection is automated or can be made part of routine operations, the collection of useful information is greatly enhanced.

Therefore, one object of the present invention capitalizes on the concept of benchmarking in the medical profession by collecting information before, during, and after a medical procedure so that the information may be analyzed and used to support changes in medical techniques and devices that are being developed or are soon to be developed.

The data collection aspect of the present invention also assists in the evaluation and modernization of standards and best medical practices used daily by medical practitioners.

In view of the foregoing, the present invention provides a system for the collection, management, and dissemination of information relating at least to a medical procedure. The system includes a user interface adapted to provide raw data information at least about one of a patient, the medical procedure, and a result of the medical procedure. At least one medical device in communication with at least the user interface is provided. The at least one medical device is adapted to receive the raw data information from the user interface, to generate operational information before, during, and after use, and optionally to transmit the raw data information and the operational information back to the user interface. A central database in communication at least with the at least one medical device is also provided. The central database is adapted to receive and tabulate the raw data information and the operational information, to select at least one related entry based on the raw data information and the operational information, and optionally to transmit the related entry to at least the at least one medical device. The at least one related entry includes information that provides at least guidance based on previously tabulated, related medical procedures. In addition, the return of information to the user may be through a totally separate path, for example a paper report or an internet web page.

The present invention also provides a system for the collection, management, and dissemination of information relating at least to adoption and use of a medical standard. The system includes a user interface adapted to provide raw data information at least about one of a patient, a medical procedure, a result of the medical procedure, and the medical standard employed during the medical procedure. At least one medical device in communication with at least the user interface is also provided. The at least one medical device is adapted to receive the raw data information from the user interface, to generate operational information before, during, and after use, and optionally to transmit the raw data information and the operational information. The system includes a central database in communication at least with the at least one medical device. The central database is adapted to receive and tabulate the raw data information and the operational information, to select at least one related entry based on the raw data information and the operational information, and optionally to transmit the related entry to at least the at least one medical device. The at least one related entry includes information that provides at least guidance based on previously tabulated information and the medical standards employed.

It is another object of the present invention to provide a method for step-wise, iterative evaluation of information relating at least to a medical procedure. The method includes providing raw data to a user interface at least about one of a patient, the medical procedure, and a result of the medical procedure, providing the raw data from the user interface to a medical device, wherein the user interface is in communication at least with the medical device, generating operational information by the medical device before, during, and after use, transmitting the raw data and the operational information from the medical device to a central database, which is in communication at least with the medical device, receiving and tabulating the raw data information and the operational information by the central database, selecting at least one related entry by the central database based on the raw data information and the operational information, and optionally transmitting the related entry to at least the medical device. The at least one related entry includes information that provides at least guidance based on previously tabulated, related medical procedures.

The present invention also provides a method for stepwise, iterative evaluation of information relating at least to employment of a medical standard. The method includes providing raw data to a user interface at least about one of a patient, the medical procedure, a result of the medical procedure, and the medical standard employed, providing the raw data from the user interface to a medical device, wherein the user interface is in communication at least with the medical device, generating operational information by the medical device before, during, and after use, transmitting the raw data and the operational information from the medical device to a central database, which is in two-way communication at least with the medical device, receiving and tabulating the raw data information and the operational information by the central database, selecting at least one related entry by the central database based on the raw data information and the operational information, and optionally transmitting the related entry to at least the medical device. The at least one related entry includes information that provides at least guidance based on previously tabulated, employed medical standards.

In one embodiment, the invention provides an interface device for collecting information relating to medical procedures. The interface device includes at least one microprocessor and a storage medium. Through the at least one microprocessor, the interface device is enabled to communicate with a fluid administration device, a scanning device, an information system and at least one other device and to receive (I) at least one of before, during and after performance of each of the medical procedures, patient identification information from at least one of the fluid administration device, the scanning device, the information system and the at least one other device and (II) automatically, at least one of during and after performance of each of the medical procedures, fluid administration information from the fluid administration device and imaging study information associated therewith from the scanning device. The at least one microprocessor matches automatically the fluid administration information with the imaging study information related thereto for each of the medical procedures performed. Associated with the at least one microprocessor, the storage medium includes a database for storing automatically as a record therein the patient identification information and the fluid administration information and the imaging study information related thereto for each of the medical procedures performed. A user interface may be used to enable an operator to interact with the interface device.

In another embodiment, the invention provides an interface device for collecting information relating to procedures. The interface device includes a microprocessor and a storage medium. Through the microprocessor, the interface device is enabled to communicate with a first device, a second device and an information system and to receive (I) at least one of before, during and after performance of each of the procedures, a set of personal identification information from at least one of the first device, the second device and the information system and (II) automatically, at least one of during and after performance of each of the procedures, a first set of procedure information from the first device and a second set of procedure information associated therewith from the second device. The microprocessor is used to match automatically the set of patient identification information with the first and the second sets of procedure information related thereto for each of the procedures performed. Associated with the microprocessor, the storage medium includes a database for storing automatically as a record therein the set of patient identification information and the first and the second sets of procedure information related thereto for each of the procedures performed.

In yet another embodiment, the invention provides a method of collecting information relating to procedures. The method includes: enabling communication with a first device and a second device; receiving at least one of before, during and after performance of each of the procedures a set of personal identification information from at least one of the first device, the second device and at least one other device; receiving automatically at least one of during and after performance of each of the procedures a first set of procedure information from the first device; receiving automatically at least one of during and after performance of each of the procedures a second set of procedure information from the second device, the second set of procedure information corresponding to the first set of procedure information obtained from the first device; matching automatically the first set of procedure information with the second set of procedure information related thereto for each of the procedures performed; and storing automatically as a record in a database the set of patient identification information and the first and the second sets of procedure information related thereto for each of the procedures performed.

Other objects of the present invention will be made apparent from the drawings and description that follows.

BRIEF DESCRIPTION OF THE DRAWINGS

Various aspects of the present invention are described in the paragraphs that follow and are illustrated by the figures below, in which.

DESCRIPTION OF THE PREFERRED EMBODIMENTS

While the present invention will be described in relation to a system and method for the development of a particular group of medical techniques, devices, and standards, it should be understood that the present invention is not limited to a system or method concerning only medical techniques, devices, and standards. As will be understood by those skilled in the art, the system and method of the present invention have wide applicability to the development of new and effective techniques, devices, and standards that may be used in medicine or any other field that may benefit from this iterative analytical tool. For example, it has been suggested that the system and method of the present invention may be utilized by wineries to improve the quality of wines through the sharing of production-related information.

Because of its far-reaching applicability, to facilitate an understanding of the present invention, the discussion that follows focuses primarily on the application of the present invention to developments related to injectors used for the injection of contrast media during certain medical diagnostic procedures.

Figure 1:
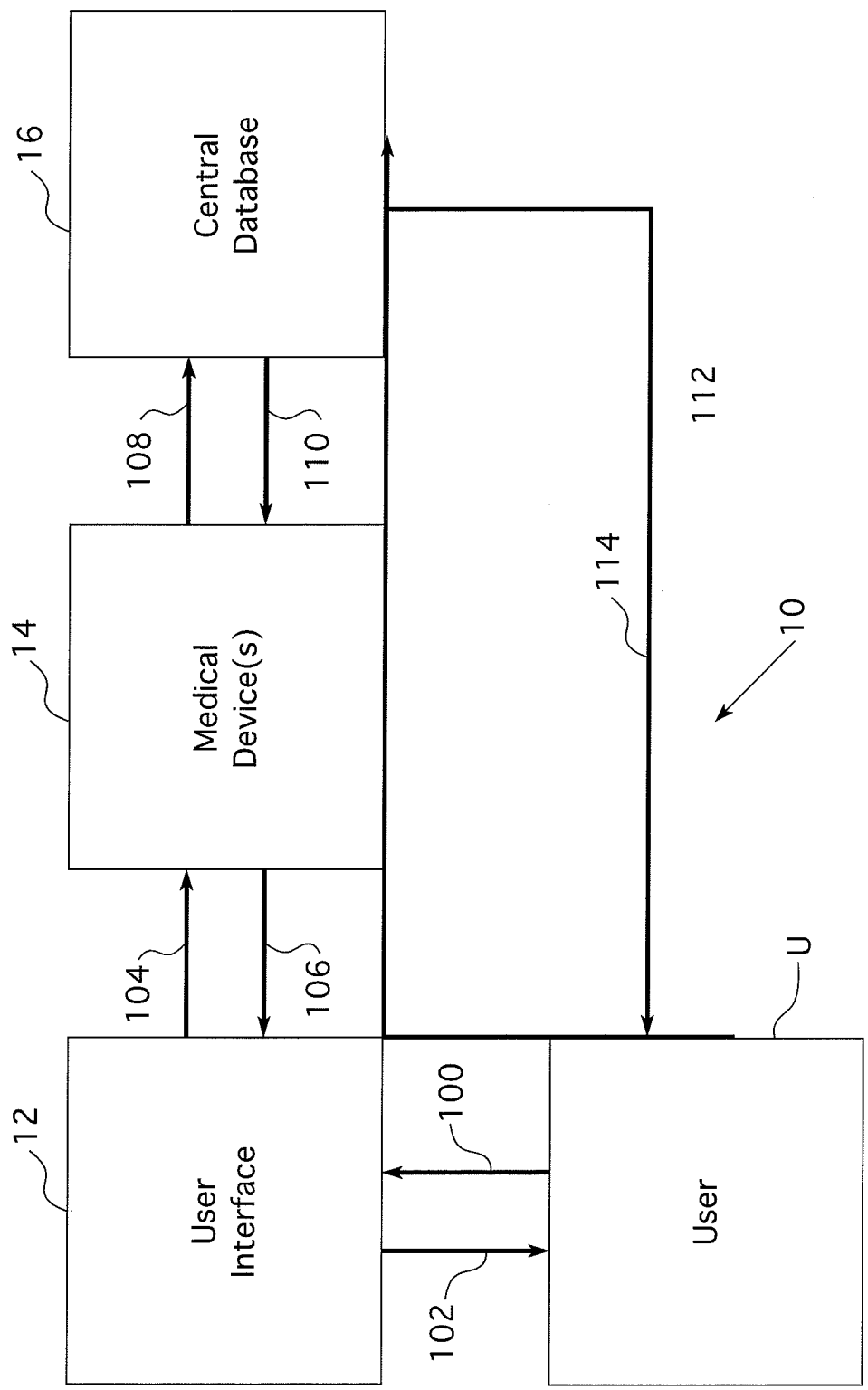
FIG. 1 is a block diagram of a first embodiment of the present invention.

FIG. 1 illustrates one embodiment of a system 10 of the present invention. System 10 includes a user interface 12 in communication with at least one medical device 14. Medical device 14, in turn, is in communication with a central database 16.

As illustrated, user U may provide input to user interface 12 through a communication link 100. When two-way communication between user U and user interface 12 is desired, user interface 12 may communicate with user U via communication link 102.

Throughout this description, communication links from one component to another will be discussed and illustrated. For clarity, the arrows indicate the direction of the communication. The arrows may be understood to indicate either separate, one-way communication links. Alternatively, they may indicate a single communication link that facilitates two-way communication. As would be appreciated by those skilled in the art, the communication link(s) may be a telephone line, a wireless communication link, or the Internet, among others.

User interface 12 may be a computer or other suitable electronic device that is capable of receiving information from an input device such as a computer keyboard. It could also be a voice recognition system. In addition, it is preferred that user interface 12 includes means for displaying or otherwise communicating information to the user. A suitable display includes a computer monitor or enunciator, among other things. Information inputted into user interface 12 is transmitted, by suitable means, indicated as communication link 104, to medical device 14, which is connected to and communicates with user interface 12 via communication link 106.

As would be understood by those skilled in the art, user interface 12 need not be a stand-alone computer in order to practice the present invention. Instead, user interface 12 may be incorporated into medical device 14 so that user interface 12 and medical device 14 are an integrated unit. When combined in this manner, user interface 12 may be an input keyboard, mouse, stylus, touch-screen, or some other suitable data input device that is manufactured as a part of medical device 14.

In the preferred embodiment of the present invention, user interface 12 is a stand-alone computer through which data may be inputted into medical device 14. User interface 12 also is preferably arranged so that information generated by medical device 14 may be communicated (via communication link 106) to user interface 12 and displayed to the user U, such as by a computer monitor, so that the practitioner or physician (the user) may monitor selected aspects of medical device 14 during its operation. Other information (for instance patient data from a Hospital Information System, or procedure data from other medical devices) related to the medical procedure may also be displayed to the user through user interface 12.

While medical device 14 is designed to receive raw data inputted through user interface 12, it is also preferably designed to generate operational information before, during, and after use. Operational information may include any number of different data types. For example, medical device 14 may operate like a flight recorder where it generates and stores real time information about its operation. Alternatively, medical device 14 may operate like a slow motion camera by generating and storing operational data on a periodic basis. Alternatively it may record the parameters of operation that were chosen by the user.

Regardless of the manner in which medical device 14 generates and stores operational information, the operational information and the raw data information are both provided from medical device 14 to central database 16 via communication link 108 where the information is collated, tabulated, and stored.

In the preferred example, central database 16 is a central computer that is capable of receiving, tabulating, and storing large quantities of information. Central database 16 is connected with medical device 14 so that they are in communication with one another via communication links 108, 110. This communication may be a hard-wired connection or it may be a wireless communication, as would be understood by those skilled in the art. For example, medical device 14 may communicate with central computer 16 through conventional telephone lines or through cellular or digital wireless channels. Alternatively, medical device 14 may communicate with central database 16 through the Internet.

While it is desirable that the user have the best practice or benchmarking data available immediately, in many situations, the information collected about procedures and outcomes does not need to be collected into the data base in real time, since it takes many cases over some time before a recommendation would be changed. In this situation, the information or data described herein could rely on physical transportation such as the postal system, other paper delivery system, or the mechanisms described in U.S. Pat. No. 5,739,508, which is incorporated herein by reference.

In addition, central database may be constructed so that it may be in communication with user U through one or both of communication links 112, 114. In this arrangement, central database 16 may communicate with user U indirectly through medical device 14 and user interface 12 or directly with user U, depending on the information type being exchanged.

It is preferred that user interface 12, medical device 14, and central computer 16 operate together to provide a seamless operation. Accordingly, it is contemplated that the three devices will operate using a single data transmission format so that the data inputted into user interface 12 or generated by medical device 14 is received easily by central database 16 and vice versa.

To that end, user interface 12 preferably communicates with medical device 14 through a connection 104, 106 whose operation is governed by a data transmission format such as the standard developed by the IEEE (Institute of Electrical and Electronics Engineers, Inc), which is known as IEEE 1073. IEEE 1073 is a standardized communication format developed specifically for use with medical devices so that those medical devices communicate with one another without the need for modifying the interface formats between them.

For example, in a hospital environment, a patient may be connected simultaneously to a number of electronic devices such as a heart monitor and a respirator. Each of these devices is controlled individually by an operating system that provides output data in a format typically recognized only by the individual device. As a result, the two separate devices traditionally operate independently of one another, because the data that they generate are in formats that are not compatible with one another.

If, however, the two devices are constructed so that the data that they generate is in the same format, the two devices could communicate with one another easily. Understandably, if the two devices could communicate with one another, the information generated by the heart monitor and the respirator potentially could be used by either device (or both devices simultaneously) to detect aberrant patient conditions that neither one of the devices could detect by itself. Without a standardized data format, such as IEEE 1073, the data from one piece of equipment must pass through a filter or "translator" so that any other equipment connected to it might understand the data that it generates.

The work on IEEE 1073 has been driven by the need to efficiently, effectively, and in a timely manner collect a comprehensive set of data related to a specific patient, to, for example, avoid adverse drug events or better manage the health care provided to that specific patient. Other Hospital Information Systems aim to efficiently, effectively, and in a timely manner collect information related to patient care, primarily for billing and reimbursement. This invention carries that work to the next level by enabling collection and analysis of data across many patients, procedures and hospitals so that future patients can benefit.

With this in mind, one aspect of the present invention contemplates that user interface 12, medical device 14, and central computer 16 will communicate with one another using a common electronic language or data format such as IEEE 1073. As would be understood by those skilled in the art, however, neither a common electronic language nor standardized communication format are required to practice the present invention. To the contrary, it is contemplated that other communication formats may be used, such as through a standard RS-232 port, so long as the devices communicate effectively with one another, especially in situations where this capability is retrofitted to previously developed devices or use with devices from different manufacturers. As would be appreciated by those skilled in the art, medical device 14 may communicate with user interface 12 through one data transmission format and communicate with the central database 16 via a second data transmission format, such as the IEEE 1073.

Each of the basic elements of system 10 (as well as the other system embodiments contemplated by the present invention) illustrated in FIG. 1 is meant to represent any of a number of different components. In other words, each element is meant to correspond to one or more devices. In addition, as noted above, the various components that may be used with the present invention are not limited to medical devices, even though the preferred embodiment is directed to medical use.

In one aspect of the present invention, medical device 14 may combine the operation of a contrast medium injector and a scanner such as a MRI scanner. User interface 12 may be a computer connected to medical device 14 to provide input to medical device 14 and to optionally receive output from medical device 14. Medical device 14 (whether one or more devices in communication with one another), in turn, communicates with a central database 16 to which medical device 14 sends information about the procedure being performed. In return, medical device 14 may receive pertinent information from central database 16 and relay that information to user interface 12 and/or user U. Alternately, medical device 14 may receive information from database 16 for its operation.

The present invention contemplates that user interface 12 and/or user U will receive potentially a large amount of information encompassing a broad spectrum of possibilities. The following discussion provides examples of at least some of the information that might be processed by the present invention, highlighting information that might be relevant to a diagnostic in which a contrast media injector and an imager (such as a MRI) are used in combination as medical device 14.

When conducting a particular medical procedure, the doctor or practitioner may input patient-specific information into user interface 12 and/or central database 16. Patient-specific information may include, for example, the weight, circulation time, age, disease (including a DRG (diagnostic related group) number that is the number used to catalog diseases much like the Dewey decimal system is used to catalog books in a library), region of study, procedure type, time since admission, image modality, contrast media type, contrast media temperature, and medication information for the particular patient. Additional examples of information that may be useful to input can be found in U.S. Pat. No. 5,840,026, which is incorporated herein by reference. The information could also include the algorithm or process that was applied to the patient-specific data to determine other parameters of the procedure.

Information about the equipment used may also be inputted into the user interface 12 and/or transmitted to central database 16. Such information may include, for example, syringe size, syringe volume, flow rate, phases, delays, the type of catheter used, and the number and type of disposables used. Equipment information may also encompass the name or type of contrast media used, the manufacturing lot for the contrast media, or the volume, density, or viscosity of the media.

Information about the imager may also be inputted through user interface 12. Imager information may include, for example, settings for the imager or scanner. Specific information about the scanner may include CT information, which may encompass such parameters as mAS (milliamp-seconds), slice thickness, speed, window, and level. The imager or scanner information also might encompass MR (magnetic resonance) imaging parameters such as time to echo, TR, NEX, FOV, slice thickness and spacing, voxel size, pulse sequence, flip angle, software version, coils used, and time of acquisition. Other imaging information such as ultrasound information or X-ray information may also be inputted into user interface 12.

Information about actuals (in contrast to information about equipment settings) may also be inputted through user interface 12 or developed in the medical device 14. Actuals include, for example, the time sequence of the procedure, the image, and the image quality of the region of interest (ROI). Actuals may also include information about hospital site data, which includes the location and size of the hospital together with the number of like procedure performed at that hospital.

Information about the results of the selected procedure may also be inputted through user interface 12 (and/or directly sent to central database 16 from user U) or developed in the medical device 14. Result-oriented information may include final results such as patient outcomes, image quality and satisfaction, quality of the study, diagnosis of the disease, diagnosis quality (e.g., the number of metastases found), user satisfaction with the equipment, information about complications, or even a final imaging report.

In addition, long-term information over multiple patients may be inputted through user interface 12 or developed in the medical device 14. Long-term information includes, for example, the usage rate of the equipment, patterns of use for the equipment, the service history of the equipment, and the reliability history of the equipment.

The foregoing list of information that may be inputted through user U, user interface 12, or developed in the medical device 14 is meant to be illustrative of the type and variety of information that system 10 of the present invention may collect, tabulate, and store. However, it is contemplated that other types of information also may be processed by the present invention. Moreover, as would be understood by those skilled in the art, the type of information inputted by user U, inputted into user interface 12, or developed in the medical device 14 depends upon the particular procedure performed.

User input through user U or user interface 12 is not the only way in which system 10 of the present invention may acquire relevant data. It is contemplated that information may be acquired by medical device 14 in an automated fashion when the information is available from a local database or computer. For example, the age, weight, disease type, and medical history of the patient may be acquired from the hospital information system (HIS) in which the procedure is performed. In this case, user interface 12 may communicate with a computer or other suitable equipment programmed to acquire information with minimal (or no) interaction by the practitioner or doctor who is performing the selected procedure.

User interface 12 communicates with medical device 14 to provide relevant information about a particular patient and procedure. Before, during and after the procedure is being performed, medical device 14 generates procedure-specific information, which is also referred to as operational information. The operational information may include a plethora of data about the procedure. The raw data information and operational information are transmitted to central database 16 where the information is collated, tabulated, and stored. After analyzing the data, central database 16 may select one or more related data entries that are relevant to the medical procedure based on certain parameters that match or are closely related among the patient raw data and procedural information inputted into central database 16.

Once selected, the one or more related data entries are relayed back to the practitioner through medical device 14 and user interface 12. Alternatively, the related data entries may be communicated directly to user U from central database 16. The related entries preferably are relayed to the practitioner before or during this or subsequent medical procedure to provide guidance to the practitioner for the medical procedure that is about to be performed or is being performed. The practitioner may be influenced by the information provided by the relevant data entries to modify the procedure.

A specific example in which system 10 of the present invention may operate is provided below.

It may be beneficial to connect an injector and an imager (or scanner) together so that they interface with one another to enhance the quality and accuracy of a final diagnostic analysis. The injector provides information about the injection (volume, flow rate, patient specific data, etc.) and relates it to a specific procedure performed (number of slices, region of interest, visibility of lesions, diagnosis, etc.). The scanner, in turn, interprets that data and performs a specific scan customary to the selected procedure. Alternatively, the scanner may be programmed to suggest how to perform a particular scan based on the information provided by the injector.

In one embodiment, the injector may be programmed to sample periodic information about the injection volume, flow rates, and patient specific information and relate that information to the procedure performed. For example, the injector may sample the scanner information on regions of the body that are of interest to the physician, the number of slices (of image cross-sections) taken, and the results of the study. It may also sample information about the outcome of the procedure, for example, the quality of the images taken, the visibility of the lesions, and the diagnosis reached by the physician.

The information collected is transmitted to a central computer or database 16 where it is compared with other like parameters (such as the patient's age, weight, health, and medical condition, etc.) for analysis. After tabulating the information, central database 16 may select one or more similar analyses performed on other occasions (called related entries) and relay that information to the practitioner so that the practitioner may use that information to the patient's benefit before or during the procedure.

If the procedure involves contrast media used for liver scans, for example, the information collected may be compared with like procedures performed across the country or around the world. Once analyzed by central database 16, the collective information may be tabulated and returned to the practitioner to help him (and the hospital) improve analytical and therapeutic techniques. For example, for a given procedure, central database 16 may return related entries that suggest a particular slice thickness, contrast volume, and/or injection rate to obtain the most accurate diagnostic result.

The same information also may help to save considerable amounts of money when treating patients. As an example, it might be learned that a particular liver scan requires on average 100 ml of contrast medium rather than the traditionally used 150 ml. The availability of this information might help a subsequent physician reduce the amount of media that is unnecessarily injected into the patient while, at the same time, reducing the cost of the procedure to the patient.

Reducing the quantity of contrast media injected into a patient also has the desired effect of increasing the safety of the diagnostic procedure. While contrast media are proven safe and effective, there is always the possibility that a patient may have an adverse reaction to the contrast media selected. If the total quantity of contrast media used may be reduced, one direct effect is that the safety of the procedure is increased because less media is injected into the patient to perform the diagnostic procedure.

Along the same lines, the same information may be used to establish new standards for performing medical procedures. If it were learned that a particular liver scan requires only 100 ml of contrast medium instead of the traditionally used 150 ml, 100 ml may be adopted as the new standard for the medical procedure. This information could be made available to users U through the system described herein, or it could be communicated through journal articles, seminars, papers at conferences, or the other communications methods currently used to reach users U.

As technology improves and the quality of scanning improves, that standard may be altered over time. For example, after central database 16 tabulates further procedures of the same type, it may be found that only 90 ml of contrast are needed (instead of the 100 ml established previously) and the standard may be altered again to reflect this. It is possible, therefore, through the iterative operation of system 10, to provide a constantly updated standard for medical procedures through the collection, tabulation, and dissemination of information about medical procedures.

In addition, the same information may be used to suggest ways in which medical equipment may be improved. For example, it may be learned through the collection and tabulation of information by system 10 of the present invention that there is a need for medical injectors to provide contrast media at a reduced flow rate, which may not be possible with existing models. With this information in hand, manufacturers may redesign the injectors that they produce to slow the injection rate, thereby providing more useful tools to practitioners that assist them in performing their daily duties.

While the general structure and operation of the present invention has been described in connection with the schematic illustrated in FIG. 1, there are several other embodiments of the present invention that are encompassed thereby.

Figure 2:
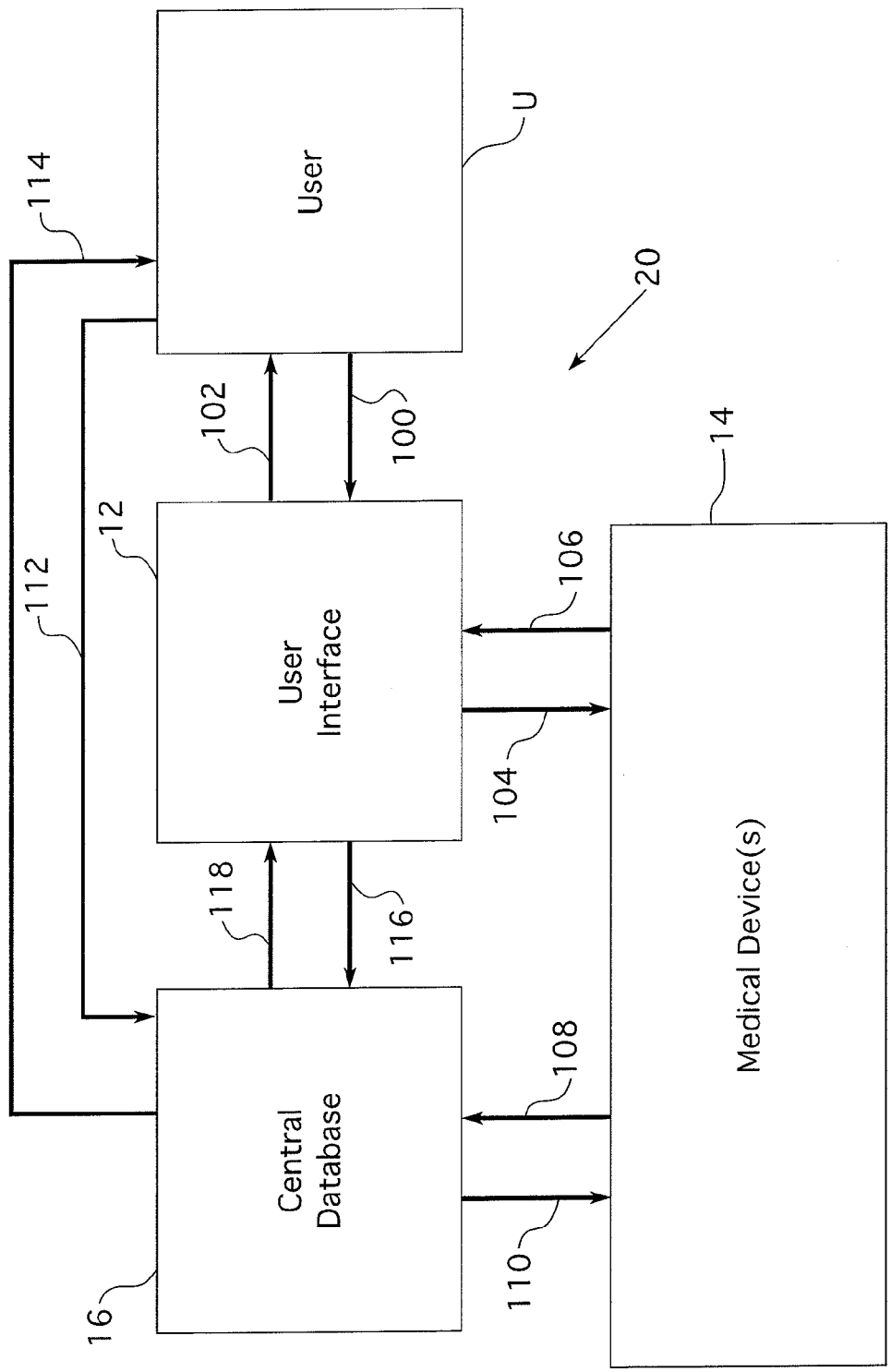
FIG. 2 is a block diagram of a second embodiment of the present invention.

For example, FIG. 2 illustrates a second embodiment of the present invention, system 20. Here, system 20 does not combine user interface 12, medical device 14, and central database 16 in series. Instead, in system 20, user interface 12, medical device 14 and central database 16 are connected in a circular arrangement so that they communicate with one another in a slightly different manner. In system 20, user interface 12 is connected by communication links 104, 106 to medical device 14 and via communication links 118, 116 to central database 16.

As illustrated in FIG. 2, user U may communicate directly with user interface 12 or central database 16 through appropriate communication links 100, 102, 112, 114. While these two communication paths are illustrated, it should be noted that user U may also communicate directly with medical device 14. To simplify the figures, this particular communication path is omitted from the FIG. 2 of the present invention.

Connected in the manner shown in FIG. 2, system 20 may operate in the same way as in the first embodiment illustrated in FIG. 1. Here, user interface 12 may provide raw data information to medical device 14, which, in turn, communicates with central database 16 (via communication links 108, 110) to retrieve related data entries. However, in this second embodiment, because user interface 12 is connected directly to central database 16 via communication links 116, 118, user U may access related data directly from central database 16 through user interface 12 without that information first being provided to medical device 14. Alternatively, user U may access and/or provide data to central database 16 through communication links 112, 114.

Figure 3:
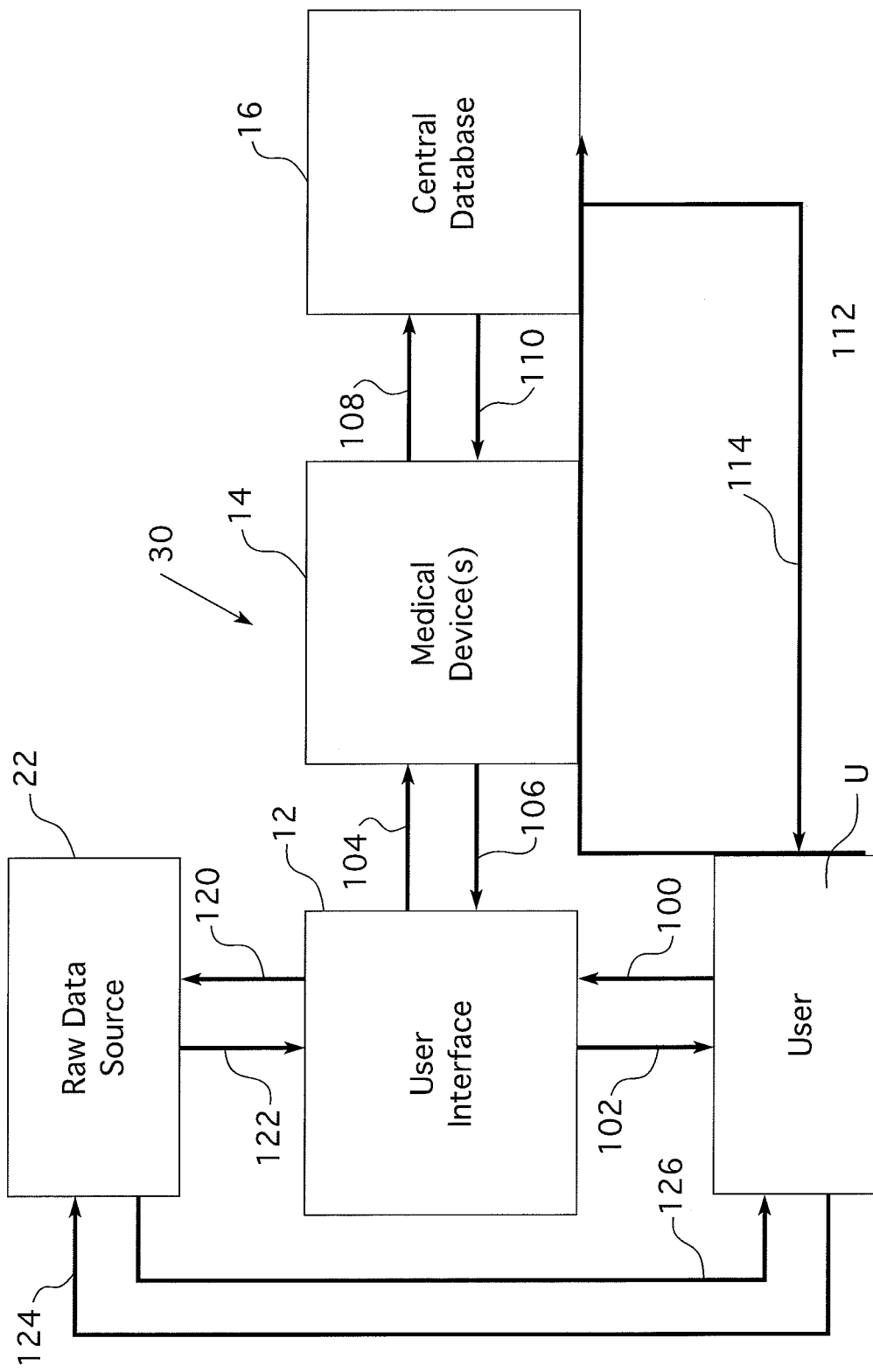
FIG. 3 is a block diagram of a third embodiment of the present invention, which is a first variation of the first embodiment illustrated in FIG. 1.

FIG. 3 illustrates system 30, which is a first variation of the first embodiment shown in FIG. 1. Here, a raw data source 22 is in communication with user interface 12 via one or both of communication links 120, 122. Raw data source 22 preferably is a database that stores information about a particular patient or procedure, among other types of information. In one aspect, raw data source 22 may be a hospital information system (HIS) in which patient-specific information and the patient's medical history are stored. The user interface 12 can request and receive information from the raw data source 22. Or, user U could interact with the raw data source 22 (via communication links 124, 126) and request that data be sent to the user interface 12 or directly to user U.

In one embodiment, it is intended that raw data source 22 be connected to user interface 12 so that user interface 12 may access the information in raw data source 22 and provide that data to medical device 14 and, ultimately, to central database 16. When raw data source 22 is provided, user U need not input all of the relevant data about a patient or procedure through user interface 12 (or to central database 16), because some of the information is provided by raw data source 22.

One anticipated benefit to the inclusion of raw data source 22 in system 30 is the automated acquisition of raw data by system 30. When raw data is acquired in an automated fashion, it is anticipated that the operation of the system of the present invention will be greatly improved, because interaction (through user interface 12, for example) by the practitioner may be greatly reduced. When the burden of inputting data through user interface 12 by the practitioner (user U) is reduced, it is anticipated that there will be a greater likelihood that pertinent raw data will be captured by system 30 than if the raw data were entered by the practitioner manually. In addition, it is expected that the raw data will be more reliable because the probability of user data entry error will be reduced.

Figure 4:
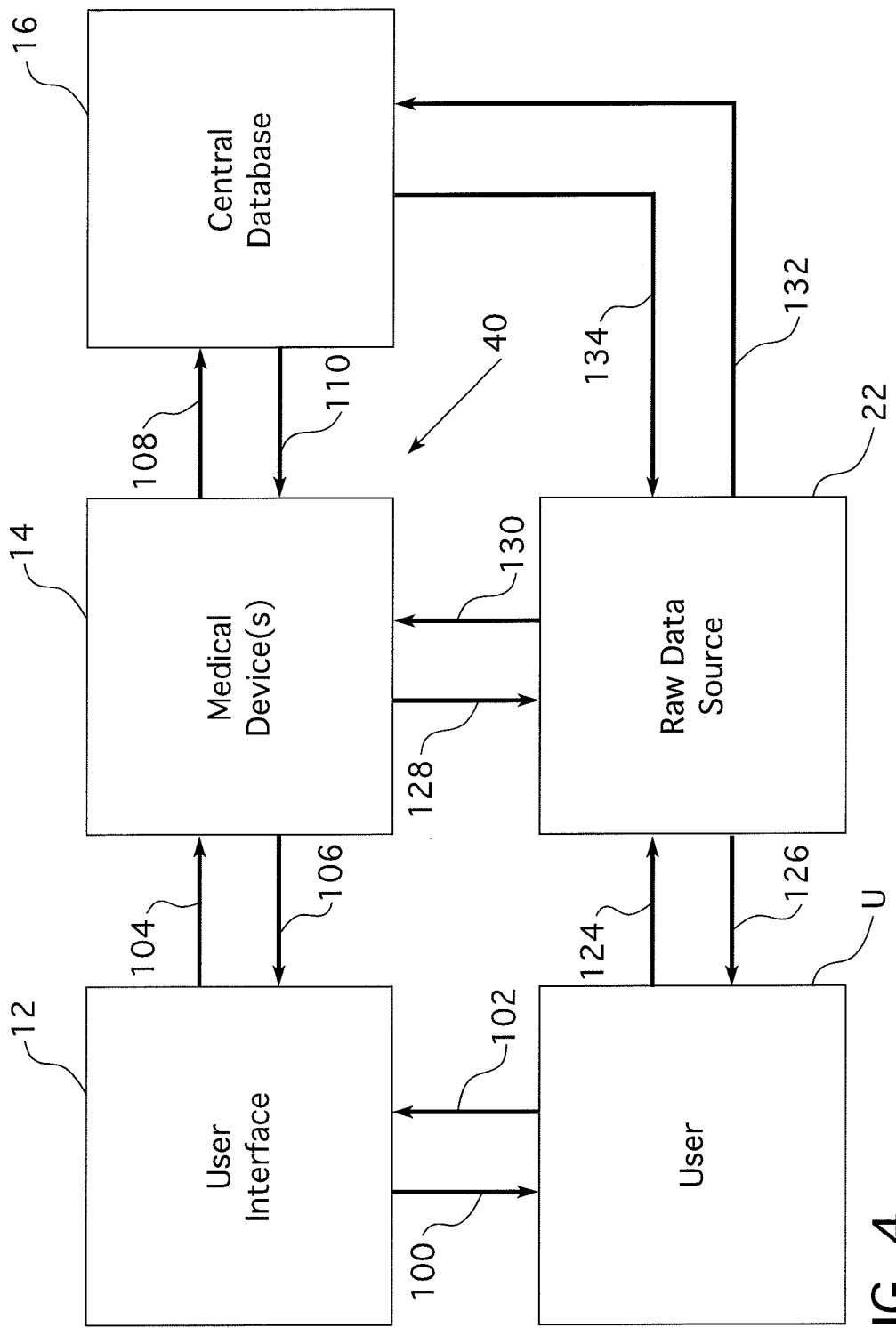
FIG. 4 is a block diagram of a fourth embodiment of the present invention, which is a second variation of the first embodiment illustrated in FIG. 1.

FIG. 4 illustrates a fourth embodiment of the present invention, system 40, which is a second variation of the first embodiment illustrated in FIG. 1. Here, system 40 operates in the same manner as the embodiments previously described except that raw data source 22 is in communication (via communication links 128, 130) with medical device 14 rather than user interface 12. In addition, raw data source 22 is in communication with central database 16 via communication links 132, 134. In this embodiment, raw data source 22 provides patient-specific information and procedure information (among other types of information) directly to medical device 14 or central database 16, leaving user interface 12 for inputting any remaining information not available from raw data source 22. Alternatively, while not illustrated, communication links may be provided from user U directly to central database 16. In all other respects, system 40 operates in the same manner as the embodiments previously described.

Figure 5:
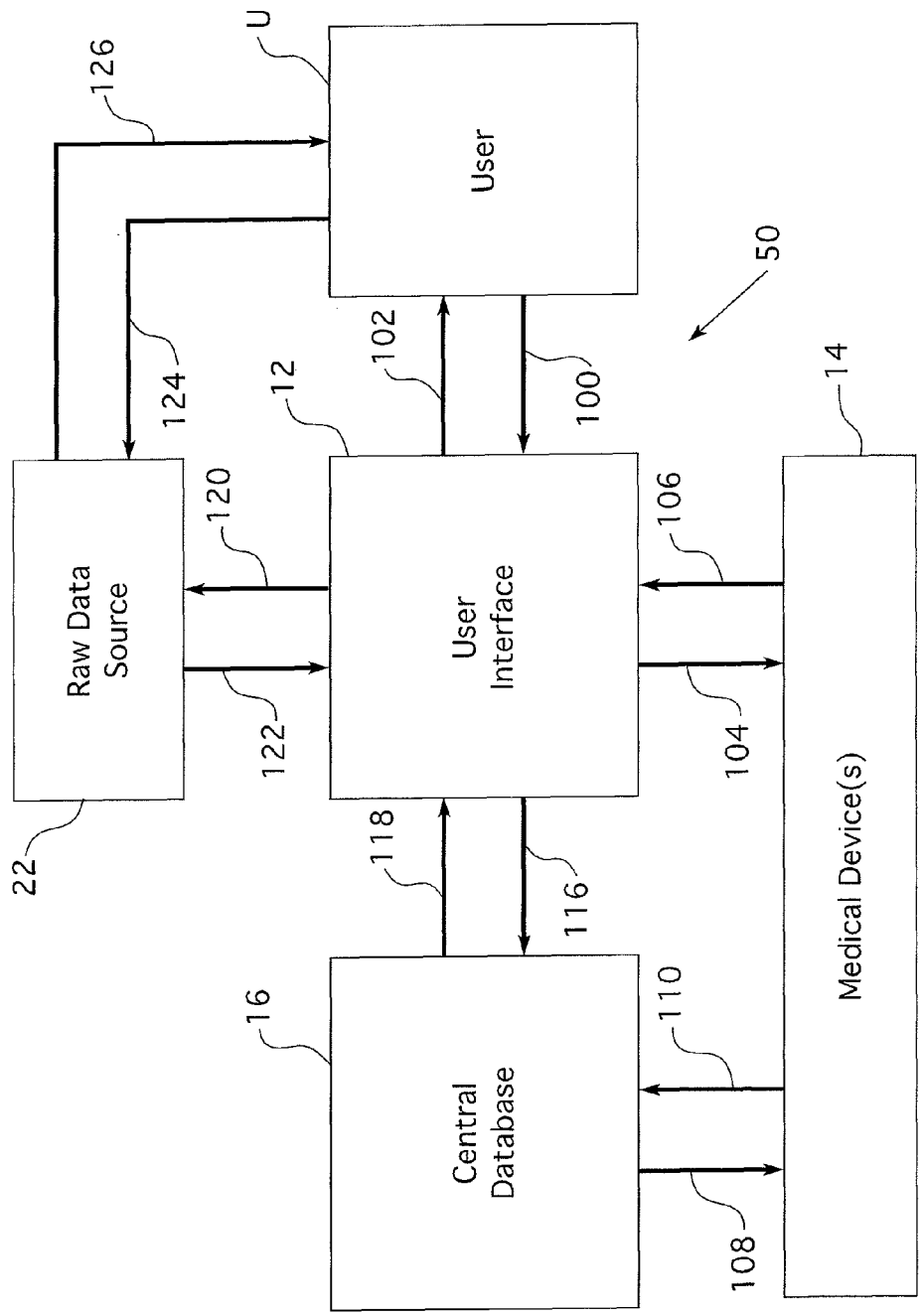
FIG. 5 is a block diagram of a fifth embodiment of the present invention, which is a first variation of the second embodiment illustrated in FIG. 2.

FIG. 5 illustrates a fifth embodiment, system 50, of the present invention, which is a first variation of the second embodiment illustrated in FIG. 2. In this embodiment, raw data source 22 is connected to user interface 12 in the same manner as with system 30 illustrated in FIG. 3. In system 50, user interface 12 is connected to central database 16 and medical device 14 in the same manner as with system 20. Raw data source 22 operates in the same manner as previously described, as does the remainder of system 50. In addition, user U is in communication with raw data source 22 via communication links 124, 126.

Figure 6:
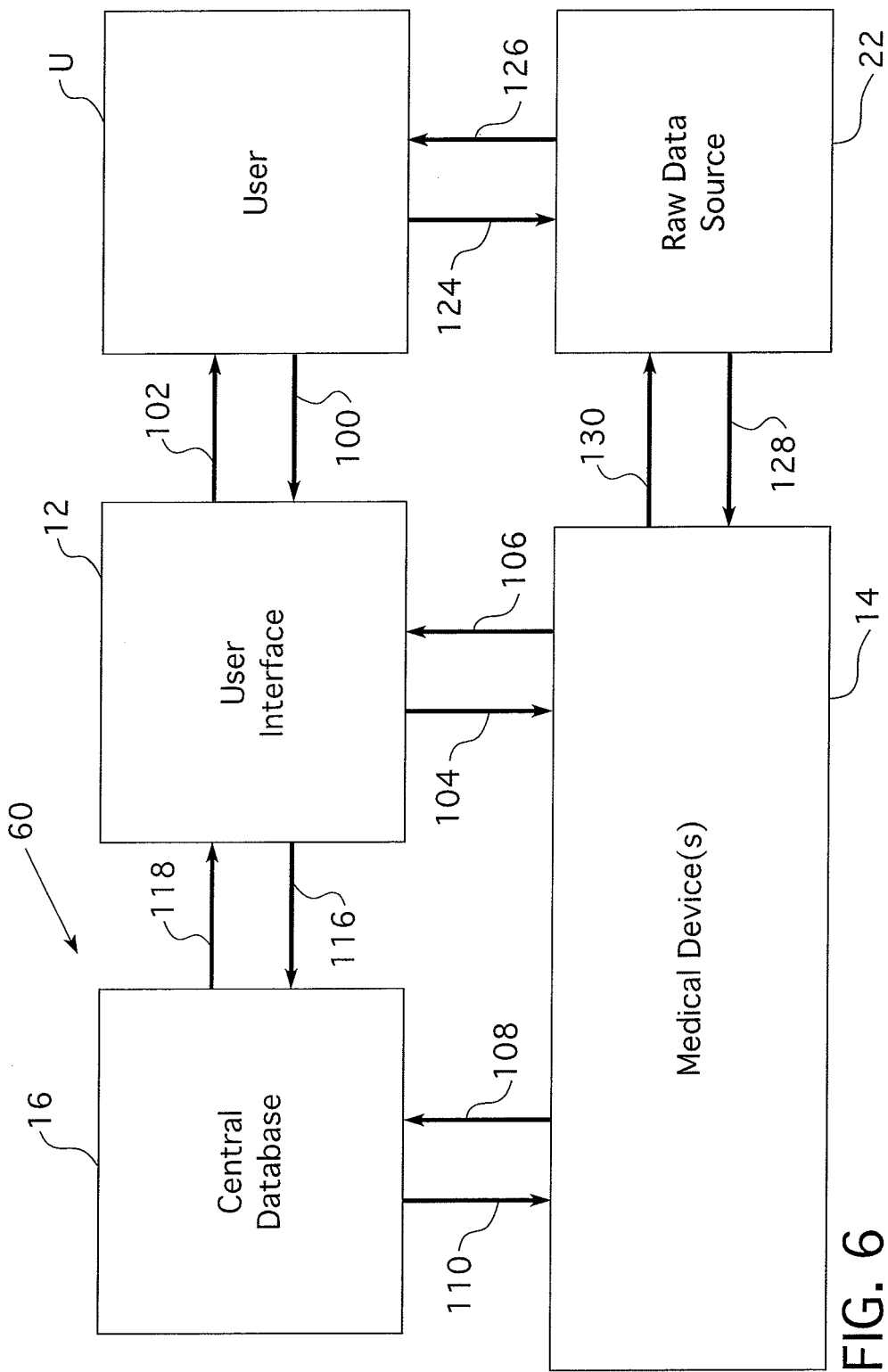
FIG. 6 is a block diagram of a sixth embodiment of the present invention, which is a second variation of the second embodiment illustrated in FIG. 2.

FIG. 6 illustrates a sixth embodiment, system 60, of the present invention. System 60 is a second variation of the second embodiment of the present invention illustrated in FIG. 2. System 60 differs from system 20 in that raw data source 22 is connected to medical device 14 (via communication links 128, 130) to input raw data into medical device 14. Moreover, user U is connected to raw data source 22 via communication links 124, 126 and also to user interface 12, as previously described. In all other respects, system 60 operates like the systems previously described.

Figure 7:
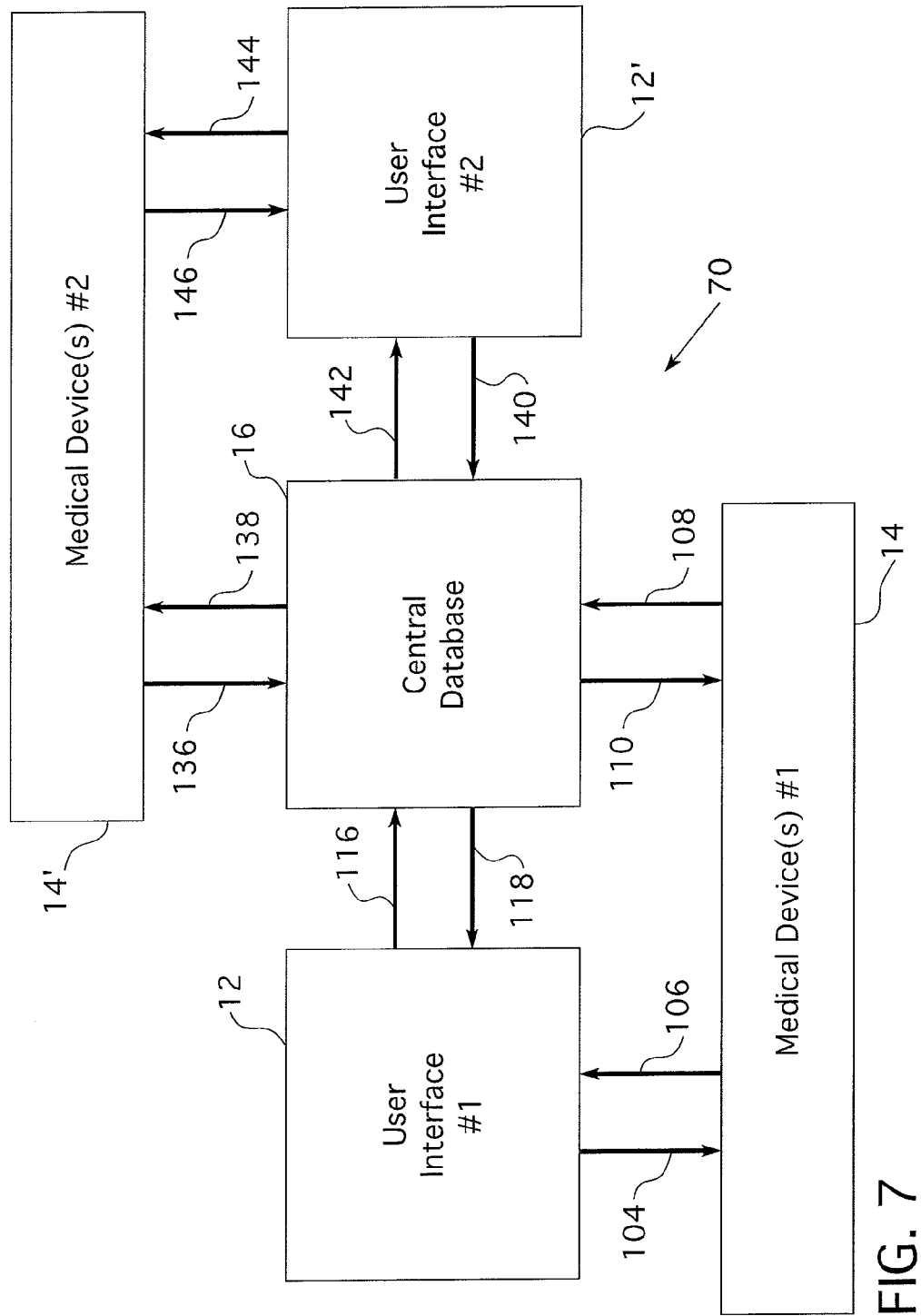
FIG. 7 is a block diagram of a seventh embodiment of the present invention, which is a third variation of the second embodiment illustrated in FIG. 2.

FIG. 7 illustrates a seventh embodiment, system 70, of the present invention. System 70 is a third variation of system 20 shown in FIG. 2. In system 70, more than one user interface 12, 12' and more than one medical device 14, 14' are shown connected to central database 16 via communication links 108, 110 and 136, 138, respectively. As discussed above, the present invention contemplates that many medical devices 14, 14' and associated input or user interface devices 12, 12' will be connected to the same central database 16 so that practitioners from around the world may share data with one another. In all other respects, system 70 operates like the previously described systems. Medical device(s) #1 14 and medical device(s) #2 14' may be different, similar, or identical devices with great or minimal physical distance between them.

Figure 8:
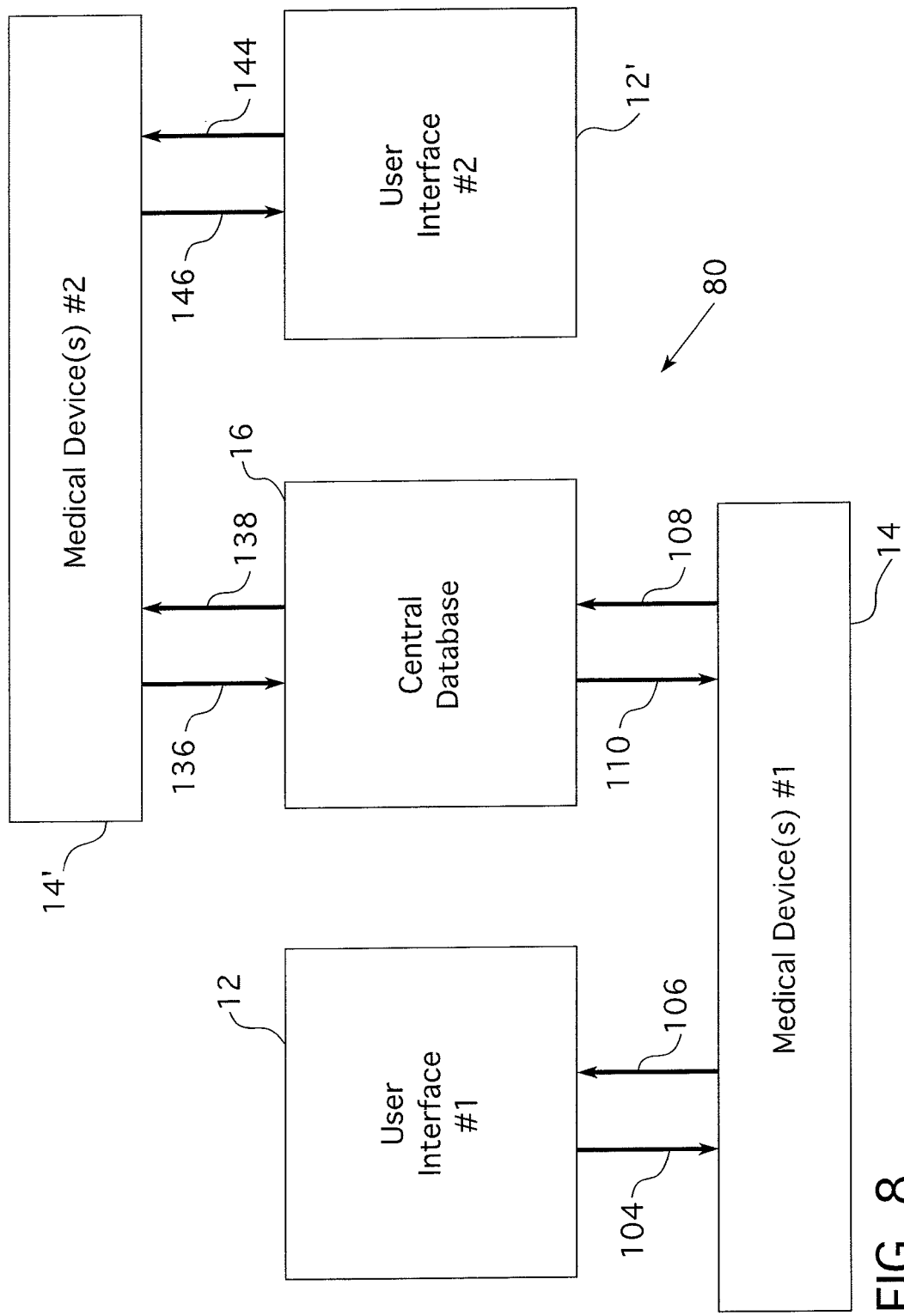
FIG. 8 is a block diagram of a eighth embodiment of the present invention, which is a third variation of the first embodiment illustrated in FIG. 1.

FIG. 8 illustrates an eighth embodiment, system 80, of the present invention. System 80 presents a third variation of system 10 illustrated in FIG. 1. In system 80, several user interfaces 12, 12' and medical devices 14, 14' are connected to central database 16 so that practitioners from around the world may share information with one another as in system 70. Here, user interface 12' is connected to medical devices #2 14' via communication links 144, 146. In all other respects, system 80 operates in the same manner as the systems previously described.

While not illustrated, in both system 70 and system 80, user U may be connected, via communication links to one or more of user interfaces 12, 12', medical devices 14, 14', a central database 16. In addition, one or more raw data sources 22 may also be connected to the systems 70, 80 as described previously.

Figure 9:
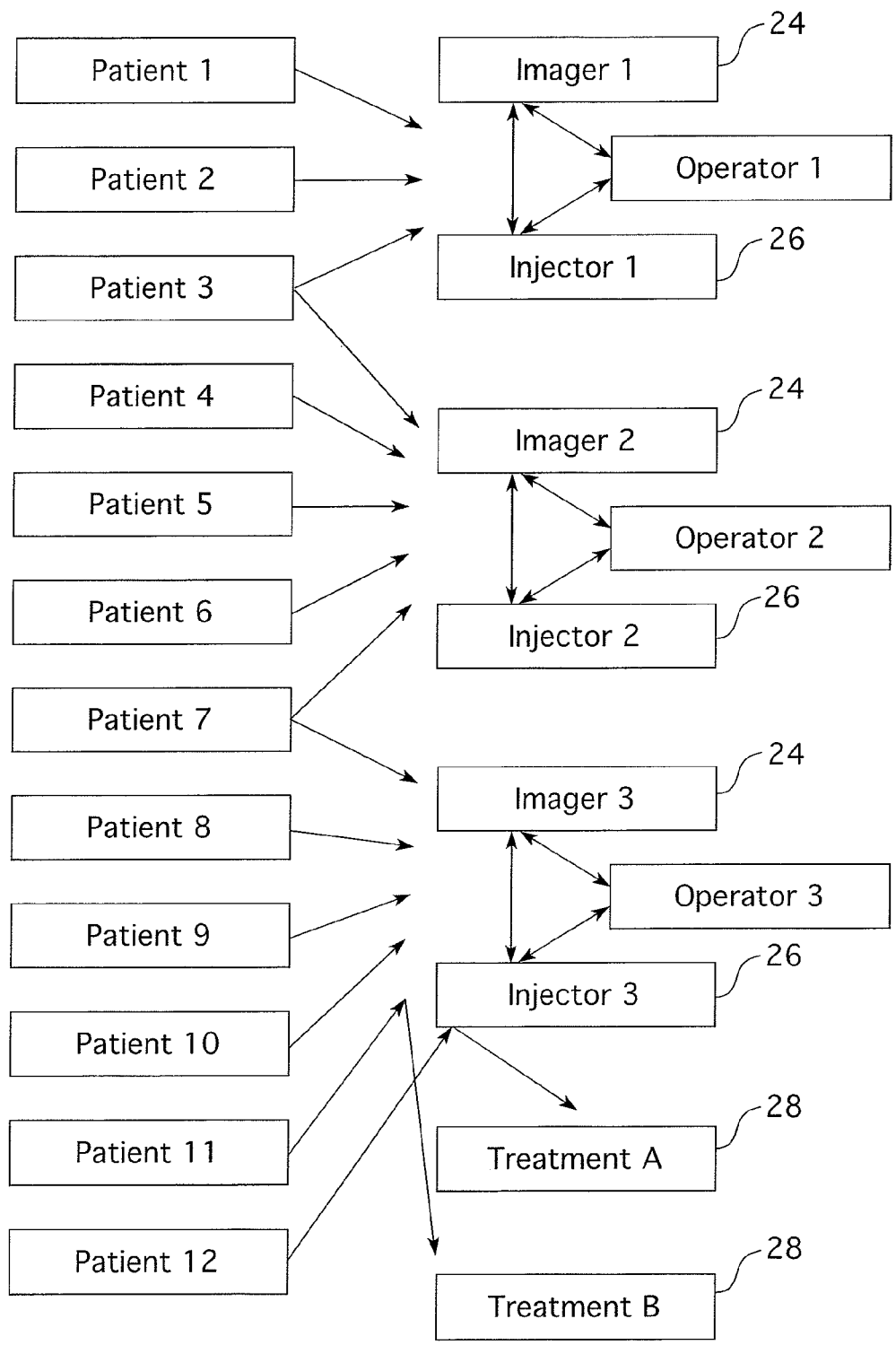
FIG. 9 is a block diagram of the interaction of several embodiments of the present invention with one another.
Figure 10:
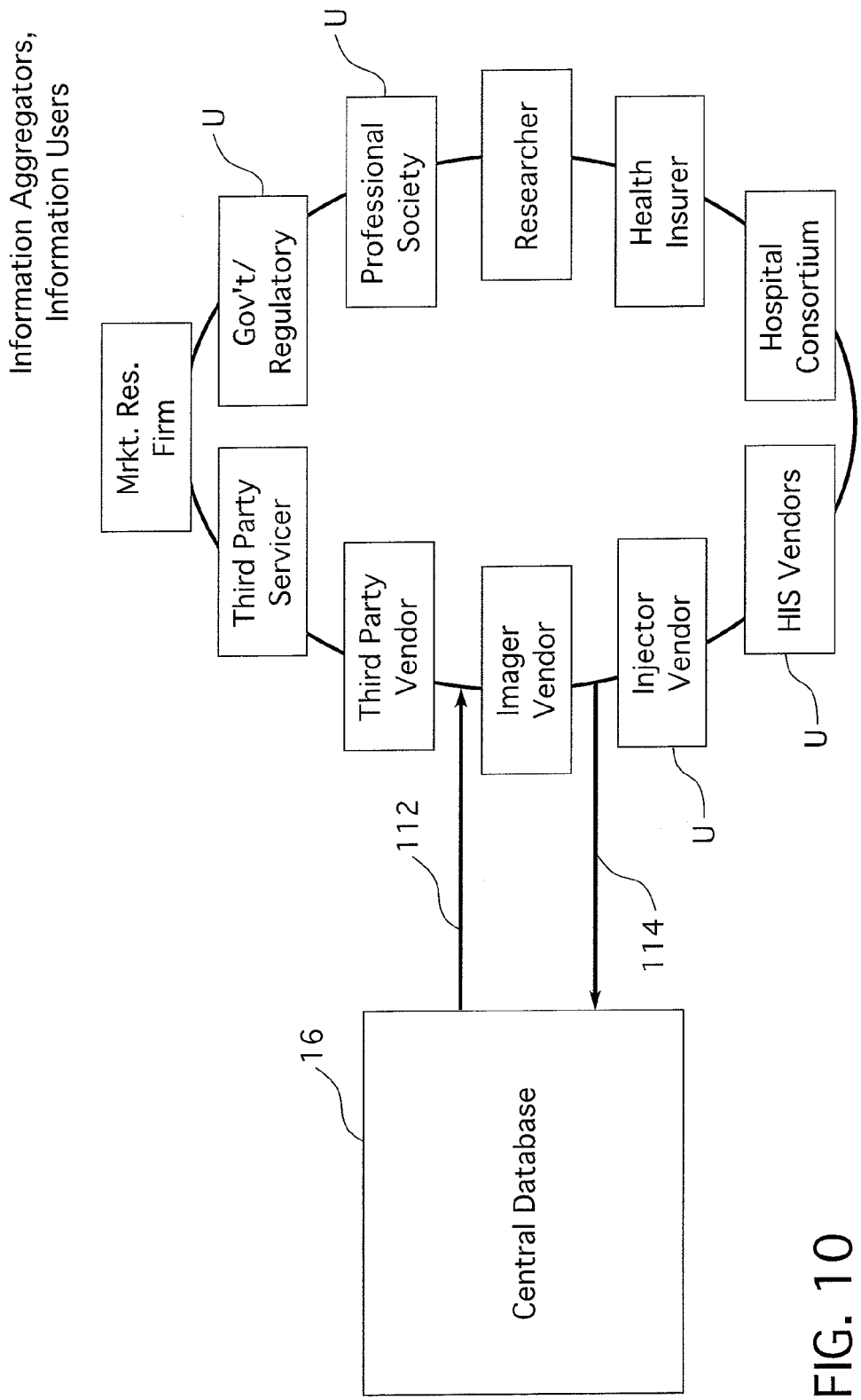
FIG. 10 is a block diagram illustrating the variety of users contemplated for the present invention.

FIG. 9 provides a schematic illustration of a system 90 according to one aspect of the present invention. Here, a number of medical devices, which are divided into imagers 24 and injectors 26, are shown in use with several patients. Imagers 24 may be of different types, for instance, MRI scanners, CT scanners, and ultrasound scanners. Different patients may have one or more imaging procedures with different equipment or the same equipment at different times. Different patients may undergo similar or different treatments 28 based upon the diagnosis made in part with the results of the imaging studies. All of the information for the various patients from the various studies and treatments 28 is preferably entered into a central database 16 using one of the systems described herein. The choice of imaging procedure and treatment for a specific patient can likewise be influenced by information available from the central database 16 through one of the systems described herein. The present invention is not limited solely to use by practitioners who wish to improve the medical techniques and standards that they employ. As FIG. 10 illustrates, any number of users U may access central database 16 to derive information relevant to that particular user's U operation. The present invention contemplates that data may be collected from any number of sources and may be accessed by any number of users U interested in that information.

For example, one user U that may rely on system 10 of the present invention may be a marketing or research firm charged with responsibility for developing new products or improving existing products. In such an instance, the marketing or research firm might incorporate software into user interface 12 or medical device 14 that collects information about the manner in which a particular medical device is used or the general reputation of the product in the particular field.

In this example, in the case of an injector 26 that has a number of functions incorporated into the memory, the software may be designed to collect information on the frequency with which practitioners rely on a particular function. If, after collecting information concerning a large number of procedures, it is determined that the function is not used with any frequency, the marketing or research firm might suggest that the function be removed from injector 26 to reduce its overall cost to the consumer.

Alternatively, a marketing or research firm might incorporate into the software for particular medical device 14 questions directed to the practitioner that prompt responses about the practitioner's satisfaction with the device. Also, the software might prompt responses designed to provide input that might assist in developing future devices. For example, the software present in either medical device 14 or in user interface 12 may ask the practitioner if injector 26 operates at an acceptable speed. Depending upon the statistical results of the query, as tabulated by central database 16, the marketing or research firm might recommend that injector 26 be modified to address the practitioners' concerns by increasing or decreasing the injection speed of injector 26.

It is also contemplated that government and regulatory agencies might be potential users U of the present invention. If so, government and regulatory agencies might work with the manufacturers to incorporate routines in the software of medical device 14 or user interface 12 to determine the frequency and efficacy of a particular medical procedure for purposes of establishing guidelines with respect to those procedures.

Alternatively, through information available through the central database 16, Medicare could determine that a particular medical diagnostic was particularly well suited to evaluating the overall health of a patient, and might add the procedure to the list of procedures that Medicare would pay for as part of its coverage.

Similarly, if the FDA were user U of the system 10 (or any other variation of system 10) of the present invention, the FDA could determine the efficacy of certain pharmaceutical compounds. To acquire this information, software might be incorporated into user interface 12 or medical device 14 to monitor patient blood levels and obtain information about the results of the use of those pharmaceutical compounds. With results tabulated over a large cross-section of the using public, the FDA could compare one compound to another to make decisions about various pharmaceuticals that are within its regulatory control.

In such an instance, the FDA might monitor statistically the occurrence of side effects for a particular compound. If the side effects of a particular drug were found to exceed acceptable limits, the FDA might rely on the data acquired to initiate an investigation of the compound or to prevent further distribution of the pharmaceutical until the safety of the drug has been fully reevaluated.

Professional societies are also contemplated as potential users of system 10 of the present invention. As organizations made up of users U, professional societies may work with the manufacturers to incorporate into the software of system 10 particular queries or data collection functions that assess the types and frequencies of procedures performed by individual members of the organization. The information collected could then be used by the professional society to determine if there are any areas in the profession or professional development that need to be addressed.

Researchers may also be a group of users U that may rely on the operation of system 10 (or any variation of system 10) to collect research information for a particular study. Using the system 10, a researcher may collect data pertinent to a particular inquiry over a large number of users U, especially if there are a large number of practitioners who are contributing data to central database 16. If so, a researcher might be able to acquire a significant amount of statistical data about a particular procedure, product, or standard that could be obtained today only through the expenditure of an enormous amount of money.

Other users U also may benefit from the operation and use of system 10 (or systems 20, 30, 40, 50, 60, 70, 80, and 90). For example, health insurers might collect information regarding a particular diagnostic procedure for purposes of determining the appropriate cost of a particular procedure. In this example, health insurers might work with the manufacturers to include in the software in user interface 12 or medical device 14 the ability to collect the costs charged for or related to a particular procedure. If so, health insurers could then compare the costs charged by particular hospitals for a particular procedure with the goal of reducing the overall cost of health care to consumers.

Hospital Consortiums, HIS vendors, injector vendors (and the manufacturers of medical device 14), imager vendors, third party vendors, and third party servicers also may be among users U of the system of the present invention. Regardless of the particular user U and the ultimate goals of that user U, in each case, user U may work with the manufacturers to incorporate into the software of system 10 routines and queries that collect a wide variety of information about particular procedures, equipment, and standards used. In this way, medical techniques, equipment, and standards may be continually updated, in an iterative fashion, as the statistical information accumulates in central database 16.

As mentioned above, the various embodiments of the system of the present invention are designed to provide an iterative analytical function that may be applied to improve medical techniques, equipment and standards. As information is collected, trends in the information can be analyzed so that best practices may be established in the medical profession, so that equipment may be updated to accommodate practitioner demands, and so that standards may be developed or refined. The various embodiments of the system of the present invention, therefore, provide an apparatus and method that collects, tabulates, and stores information that can be accessed in a selective manner to disseminate information to practitioners with the ultimate goal of improving the quality of health care.

While the word "central" in central database 16 might imply to the reader a central physical location, with current rapid improvements in information technology, this is no longer an implementation requirement. It is possible to have a database that is distributed among many computers at one site, at various sites around the country, or even around the world. It is also possible for the data to reside on various medical devices 14. In this case, an inquiry may poll the various medical devices 14 to get the information only when it is needed for a response. Or an inquiry could "launch" a request, and the request could travel from medical device 14 to medical device 14, gathering the necessary information along the way. The essential function of the central database 16 is to provide a way to collect the appropriate data in response to an inquiry. As new information technologies are developed, they can be used to perform this central database function. For example, users U may be able access central database 16 via an internet interface to create inquiries.

There are also other methods for medical practitioners to receive and be influenced by the information and analyses derived from this invention in addition to the user interface 12. The results of an inquiry can be published in an electronic or paper format by a manufacturer, a professional organization, or the FDA. Or, they can be incorporated into standards, reimbursement policies, or practice guidelines that are subsequently published in some form. Or medical practitioners may access them through the Internet. The information also can be incorporated into in-service training conducted by the medical device manufacturer(s) or seller(s).

In all of the above system descriptions, direct communication paths are shown between specific system elements. Given the communications infrastructure of today and the possibilities of future developments, the specific communication path may be circuitous or indirect. The operation of the present invention results in information being transmitted from one place to the other in a reliable and timely manner. The details of the path route or technology used are inconsequential. The benefits of this invention for information communication and use are not limited by the specifics of physical connectedness. For instance, communications path 114 in FIG. 1 can be a paper article or written procedure recommendation in situations where such a response is sufficient. As a second example, medical device 14 may communicate with central database 16 through user interface 12. The fact that medical device 14 communicates with central database 16 though a third device or devices, either shown or not shown, is within the scope of this invention. Thus the various communications paths show in FIG. 1 through 8 are some from among many possibilities.

Also, all the communication paths are preferably, but not necessarily, two-way. When user U interacts with user interface 12, there is normally a two-way communication, because user U prefers feedback to know that what was provided was the input that was desired (that user U pressed the right key, for instance). Normally, the communications between two devices involves at least the two-way communications embodied in the RS-232 protocol. More commonly, there is some type of acknowledgement message sent to confirm satisfactory transmission of the information from one device to another. However, there are examples, such as the remote reading of water meters where the communication in one direction is as simple as a signal to indicate "send your data," and there is no acknowledgement that the data is subsequently received.

FIG. 11 contains plots of data collected to support an analytical example to illustrate the usefulness and power of the system described herein to improve medical practice and the design of medical products. The plots are of hypothetical data that have been collected in central database 16 from many similar medical procedures over time.

Figure 11A:
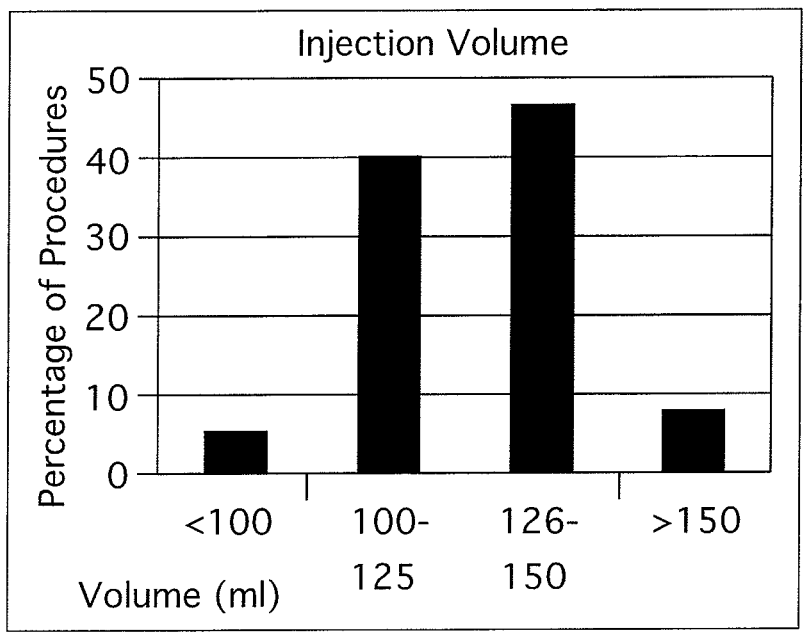
FIGS. 11A-11E provide selected details of one example application of the present invention.

FIG. 11A shows a histogram of contrast injection volumes for a CT study looking for cancer metastases to the liver. Almost all procedures are performed with doses between 100 and 150 ml. The volume of the injection is a piece of data that the user selects through user interface 12. This data is then sent to medical device 14, in this case the injector. From there it goes to central database 16.

Through a second medical device 14, the CT image is taken and if metastases are seen, they can be indicated on the image by the user and their image contrast level is compared to that of the normal liver tissue. In CT imaging, the image contrast is measured in Hounsfield units. To simplify the display of the data, the contrast is grouped into 4 classes, 1, 2, 3, and 4. This image contrast of the metastases is then communicated to central database 16.

Figure 11B:
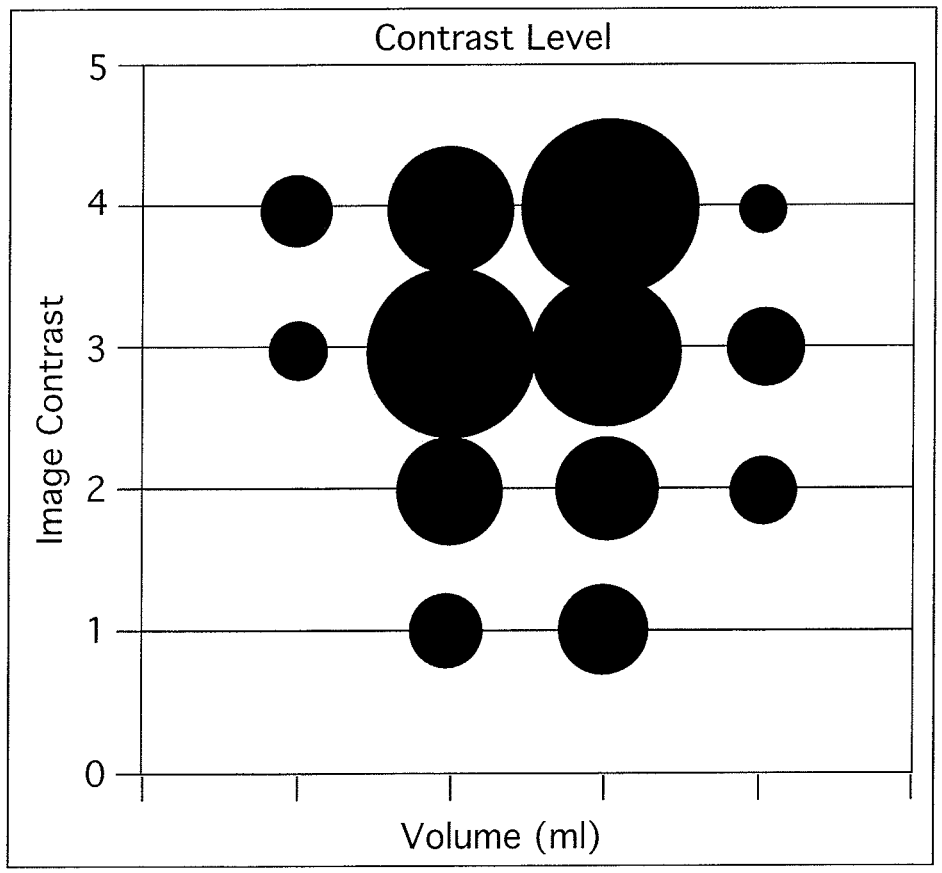

FIG. 11B is a bubble chart showing the relationship between image contrast and volume of contrast injected for a number of studies. The size of the bubble shows the relative occurrence of that image contrast level given an injection of a specified volume of contrast media. While greater volumes may be said to give slightly more image contrast, there is really no quantifiable relationship between the two. The few very low volume injections produce image contrast in the 3 and 4 range and a few injections with volume in the highest range produced image contrast at level 2.

Figure 11C:
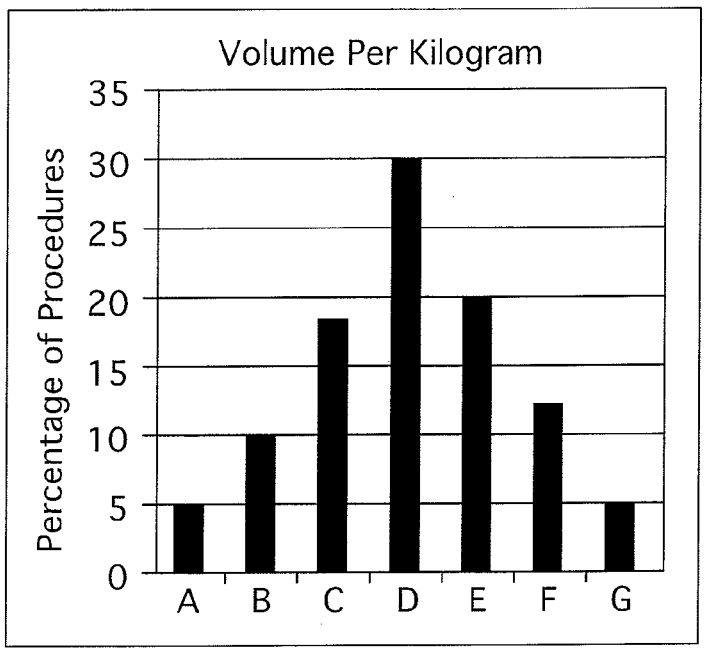

Information about the patients' weights can increase the benefit of the analysis. The patient's weight information can be entered by user U through user interface 12 or can be retrieved from raw data source 22. It is then sent to the central database 16. FIG. 11C shows the distribution of procedures with the various volumes of contrast per kilogram weight of the patient. As shown, the curve is approximately normal with a slight skewing to the high side. When the bubble chart is replotted with image contrast as a function of volume contrast per kilogram as in FIG. 11D, there is a clear relationship between the two, although there are still other factors that affect the relationship. Regression analysis could be applied to determine the strength of this relationship and to test the strengths of the effect of other factors, for instance imaging equipment type or settings, or patient circulatory system health or state of compromise.

By asking user U, after the procedure, to rate the confidence of their diagnosis after the procedure through user interface 12, it is possible to learn more and further improve the medical procedure. The user's assessment of their confidence in the diagnosis is sent to central database 16. FIG. 11E shows the relationship between diagnosis confidence on a 4-point scale and image contrast, also on a 4-point scale. In almost all cases, and image contrast of 3 or 4 gives a diagnosis confidence of 3 or 4.

Figure 11D:
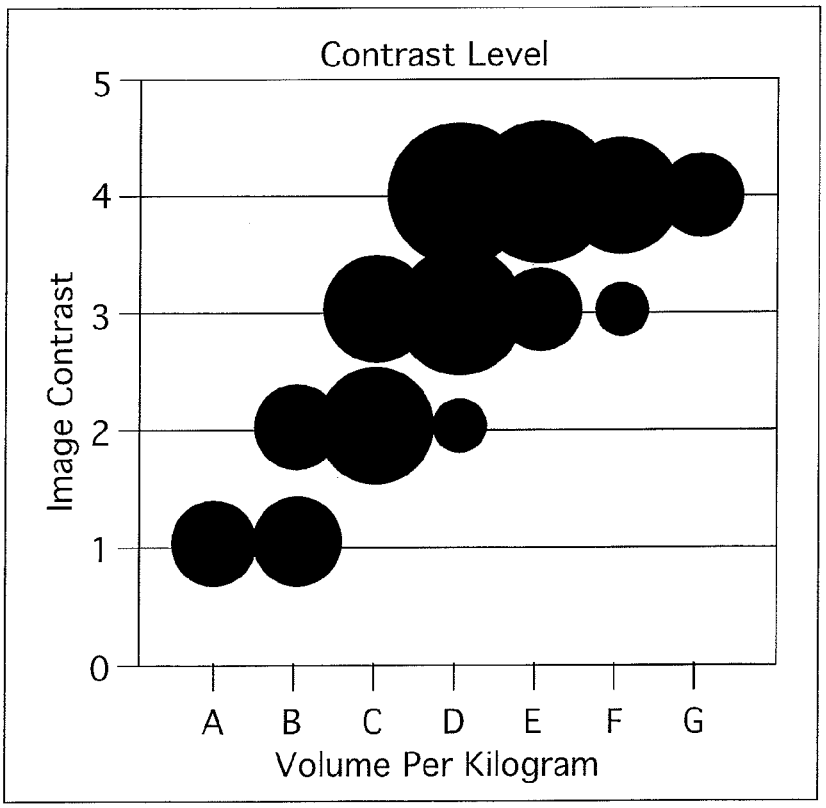
Figure 11E:
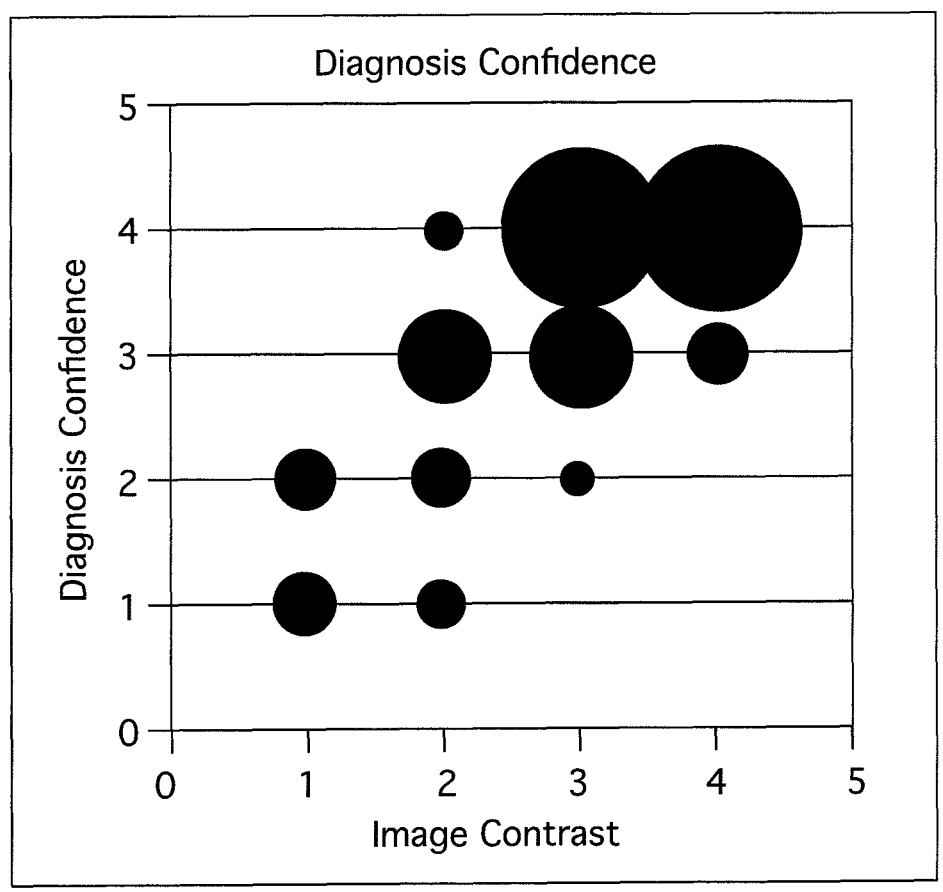

This information can be used in conjunction with FIG. 11D to develop a practice recommendation. In this example, the recommendation would be that there is no need for any contrast doses above level E because this volume per kilogram yields image quality sufficient for a high diagnosis confidence. Also, the recommendation would be that doses at or below level C should be avoided. There is some option among levels D and E. Level E guarantees, aside from human error, a sufficient image contrast to make a confident diagnosis. Level D has a small chance of producing a diagnosis confidence level of 2 or 1. If the other significant factors could be determined and controlled, then contrast level D could be recommended. There is considerable cost savings improvement available by avoiding giving more contrast than needed—levels F and G. And, by avoiding levels A through C, the chance of misdiagnosis or having to repeat the study can be significantly reduced, also improving the quality of health care and reducing costs.

As mentioned earlier, this information and analysis can also be very useful to manufacturers as they design improved products. In this case, the recognition that volume per kilogram is the most important factor in determining image contrast and, thus, diagnosis confidence could indicate that a fluid injector system needs to be designed to allow much more flexible dosing that is currently available with prefilled syringes of a single size and contrast bottle which are available primarily in 25 ml increments.

Related data is the term applied to data derived from the original data placed into central database 16. Related data is preferably stored in central database 16 for ease of access, but in the spirit of distributed databases, it may be stored elsewhere or derived as needed. In the example related through FIG. 11, related data is the histogram of occurrence of the various volumes per kilogram, and the 3 bubble plots of 11B, 11D, and 11E.

While the invention has been described by way of exemplary embodiments, it is understood that the words which have been used herein are words of description, rather than words of limitation. For example, medical standards are not limited to formally approved standards. It includes best practices or simply standard or common practices of an organization, a particular imaging suite, or an individual. Also, the designations before, during and after are meant to indicate expected or common practice. A user can enter all the information after use, although they cannot enter all the information before use, since the results of the procedure cannot be known until the procedure is performed. Changes may be made, within the purview of the appended claims without departing from the scope and the spirit of the invention in its broader aspects.

What is claimed is:

1. An interface device for collecting information relating to medical procedures, the interface device comprising:
   (a) a user interface for an operator of said interface device to interact therewith;
   (b) a microprocessor through which said interface device is enabled to communicate with a fluid administration device, a scanning device, an information system and at least one other device, wherein the microprocessor is configured to receive:
      (I) patient identification information from at least one of said user interface, said scanning device, said information system and said at least one other device, and
      (II) automatically, at least one of during and after performance of a medical procedure, fluid administration information from said fluid administration device and imaging study information associated therewith from said scanning device, the microprocessor matching automatically the fluid administration information with the imaging study information related thereto for each of the medical procedures performed; and
   (c) a storage medium associated with said microprocessor, the storage medium having a database for storing automatically as a record therein the patient identification information, the fluid administration information and the imaging study information related thereto for each of the medical procedures performed for use by the operator thereof.

2. The interface device of claim 1 further including a communications link for establishing communication with a central computer through which one or more of the records stored in said database can be optionally transmitted to said central computer for use thereby.

3. The interface device of claim 2 wherein said communications link is configured to establish communication between said interface device and said central computer at least in part through a network.

4. The interface device of claim 3 wherein said network includes the Internet.

5. The interface device of claim 2 wherein the interface device is configured to generate operational information pertaining thereto at least one of before, during, and after each use thereof and to transmit, via said communications link, the operational information to said central computer.

6. The interface device of claim 5 wherein the interface device is configured to display the operational information via said user interface.

7. The interface device of claim 2 wherein the interface device is configured to receive operational information from at least one of said fluid administration device, said scanning device, said information system and said at least one other device and to transmit, via said communications link, the operational information to said central computer.

8. The interface device of claim 2 wherein the interface device is configured to receive equipment information about equipment used by said fluid administration device and to transmit, via said communications link, the equipment information to at least one of a vendor thereof and said information system, the equipment information including at least one of a size of a syringe used, a volume of the syringe used, a type of a fluid used, a manufacturing lot of the fluid used, a rate of flow of the fluid used, a volume of the fluid used, a type of a catheter used, and, generally, a number of disposables used.

9. The interface device of claim 1 wherein said at least one other device includes one of a second fluid administration device, a second scanning device, a second information system, a separate user interface and a second interface device.

10. The interface device of claim 2 wherein said user interface includes at least one of:
   (a) a keyboard for entering into said interface device at least one of patient-specific information and the patient identification information;

(b) a mouse for entering into said interface device at least one of the patient-specific information and the patient identification information;

(c) a barcode reader for entering into said interface device at least one of the patient-specific information and the patient identification information;

(d) a touch-screen for entering into said interface device at least one of the patient-specific information and the patient identification information;

(e) a monitor for displaying at least one of the patient-specific information, the patient identification information, the fluid administration information and the imaging study information of at least one of the records; and (f) a printer for printing at least one of the patient-specific information, the patient identification information, the fluid administration information and the imaging study information of at least one of the records.

11. The interface device of claim 8 wherein the user interface is configured to permit entry therein of an algorithm to apply to at least some of the records in the database and to determine therefrom result-oriented information based thereon for communication via said communications link to said central computer.

12. The interface device of claim 1 wherein the interface device is configured to receive the patient identification information automatically from at least one of said fluid administration device, said scanning device, said information system and said at least one other device.

13. The interface device of claim 2 wherein the interface device is configured to receive, from said central computer via said communications link information affecting operation of said interface device for use thereby.

14. The interface device of claim 2 wherein the interface device is configured to receive, via said communications link, information from a vendor of at least one of said fluid administration device, said scanning device, said information system and said at least one other device for use thereby.

15. The interface device of claim 1 wherein the patient identification information includes at least one of a patient name, a patient age, a patient weight, a patient health, a patient medical condition, a disease type and a patient medical history.

16. The interface device of claim 1 wherein the fluid administration information includes at least one of a flow rate of administration, a volume administrated, a type of contrast media, a density of the contrast media, a viscosity of the contrast media, a manufacturing lot for the contrast media, a temperature of the contrast media, a syringe size, a syringe volume, a phase of administration, an administration start time, an administration end time, and a delay.

17. The interface device of claim 1 wherein the imaging study information includes at least one of an imaging modality, a region of study, a type of study, a quality of study, an image of study, a study start time, a study end time, and a final imaging report.

18. The interface device of claim 1 wherein the imaging study information includes scanning device parameters for said scanning device, the scanning device parameters including at least one of a number of slices, a slice thickness, a slice spacing, a speed, a window, a level, a time to echo, a field of view, a voxel size, a pulse sequence, a flip angle, a software version, a number of coils used, a time of acquisition, a milliamp-seconds calculation, and X-ray information.

19. The interface device of claim 2 wherein the interface device is configured to receive, via said communications link, updated software for operation thereof from at least one of said central computer and a vendor of said interface device.

20. The interface device of claim 2 wherein the interface device is configured to transmit, via said communications link, statistical information about operation of at least one of said fluid administration device, said scanning device, said information system and said at least one other device received therefrom, wherein the statistical information includes at least one of a usage rate, a pattern of use, a service history and a reliability history of at least one of said fluid administration device, said scanning device, said information system and said at least one other device.

21. The interface device of claim 1 wherein said information system is a hospital information system.

22. An interface device for collecting information relating to medical procedures, the interface device comprising:

(a) at least one microprocessor through which said interface device is enabled to communicate with a fluid administration device, a scanning device, an information system and at least one other device, wherein the at least one microprocessor is configured to receive:

(I) at least one of before, during and after performance of each of the medical procedures, patient identification information from at least one of said fluid administration device, said scanning device, said information system and said at least one other device, and (II) automatically, at least one of during and after performance of each of the medical procedures, fluid administration information from said fluid administration device and imaging study information associated therewith from said scanning device, wherein the at least one microprocessor automatically matches the fluid administration information with the imaging study information related thereto for each of the medical procedures performed; and (b) a storage medium associated with said at least one microprocessor, the storage medium having a database for storing automatically as a record therein the patient identification information and the fluid administration information and the imaging study information related thereto for each of the medical procedures performed for use by a user thereof.

23. The interface device of claim 22 wherein said at least one microprocessor is further configured to receive the patient identification information automatically from at least one of said fluid administration device, said scanning device, said information system and said at least one other device.

24. The interface device of claim 22 further including a user interface, the user interface including at least one of:

(a) a keyboard for entering into said interface device at least one of patient-specific information and the patient identification information;

(b) a mouse for entering into said interface device at least one of the patient-specific information and the patient identification information;

(c) a barcode reader for entering into said interface device at least one of the patient-specific information and the patient identification information;

(d) a touch-screen for entering into said interface device at least one of the patient-specific information and the patient identification information;

(e) a monitor for displaying at least one of the patient-specific information, the patient identification information, the fluid administration information and the imaging study information of at least one of the records; and (f) a printer for printing at least one of the patient-specific information, the patient identification information, the fluid administration information and the imaging study information of at least one of the records.

25. The interface device of claim 22 further including a communications link, wherein said communications link is configured to establish at least one of:
(a) a transmission to a central computer for use thereby of one or more of the records stored in said database;
(b) a reception from said central computer of information affecting operation of said interface device for use thereby;
(c) a transmission to said central computer of operational information pertaining to said interface device at least one of before, during, and after each use thereof;
(d) a reception of updated software for said interface device from at least one of said central computer and a vendor of said interface device;
(e) a reception of information from a vendor of at least one of said fluid administration device, said scanning device, said information system and said at least one other device for use thereby;
(f) a transmission to said central computer of statistical information about operation of at least one of said fluid administration device, said scanning device, said information system and said at least one other device received therefrom, the statistical information including at least one of usage rate, patterns of use, service history and reliability history of at least one of said fluid administration device, said scanning device, said information system and said at least one other device;
(g) a transmission to said central computer of operational information received from at least one of said fluid administration device, said scanning device, said information system and said at least one other device; and
(h) a transmission to at least one of said information system and a vendor of said fluid information device of information about equipment used by said fluid administration device, the equipment information including at least one of a size of a syringe used, a volume of the syringe used, a type of a fluid used, a manufacturing lot of the fluid used, a rate of flow of the fluid used, a volume of the fluid used, a type of a catheter used, and, generally, a number of disposables used.

26. The interface device of claim 25 further including a user interface configured to at least display at least one of the operational information, the statistical information and the equipment information.

27. The interface device of claim 22 further including an algorithm for processing the records stored in the database so as to determine therefrom result-oriented information based thereon for communication to at least a central computer.

28. The interface device of claim 22 wherein the fluid administration information includes at least one of a flow rate of administration, a volume administered, a type of contrast media, a density of the contrast media, a viscosity of the contrast media, a manufacturing lot for the contrast media, a temperature of the contrast media, a syringe size, a syringe volume, a phase of administration, an administration start time, an administration end time, and a delay.

29. The interface device of claim 22 wherein the imaging study information includes at least one of an imaging modality, a region of study, a type of study, a quality of study, an image of study, a study start time, a study end time, and a final imaging report.

30. The interface device of claim 22 wherein the imaging study information includes parameters for said scanning device, the scanning device parameters including at least one of a number of slices, a slice thickness, a slice spacing, a speed, a window, a level, a time to echo, a field of view, a voxel size, a pulse sequence, a flip angle, a software version, a number of coils used, a time of acquisition, a milliamp-seconds, calculation, and X-ray information.

31. The interface device of claim 22 wherein said information system is a hospital information system.

32. An interface device for collecting information relating to procedures, the interface device comprising:
(a) a microprocessor through which said interface device is enabled to communicate with a first device, a second device and an information system, wherein the microprocessor is configured to receive:
(I) at least one of before, during and after performance of each of the procedures, a set of personal identification information from at least one of said first device, said second device and said information system, and
(II) automatically, at least one of during and after performance of each of the procedures, a first set of procedure information from said first device and a second set of procedure information associated therewith from said second device,
wherein the microprocessor automatically matches the set of patient identification information with the first and the second sets of procedure information related thereto for each of the procedures performed; and
(b) a storage medium associated with said microprocessor, the storage medium having a database for storing automatically as a record therein the set of patient identification information and the first and the second sets of procedure information related thereto for each of the procedures performed for use by a user thereof.

33. The interface device of claim 32 further including a user interface, the user interface including at least one of:
(a) a keyboard for entering into said interface device at least one of patient-specific information and the patient identification information;
(b) a mouse for entering into said interface device at least one of the patient-specific information and the patient identification information;
(c) a barcode reader for entering into said interface device at least one of the patient-specific information and the patient identification information;
(d) a touch-screen for entering into said interface device at least one of the patient-specific information and the patient identification information;
(e) a monitor for displaying at least one of the patient-specific information, the patient identification information, the first set of procedure information and the second set of procedure information of at least one of the records; and
(f) a printer for printing at least one of the patient-specific information, the patient identification information, the first set of procedure information and the second set of procedure information of at least one of the records.

34. The interface device of claim 32 wherein said first device is a contrast medium injector and the first set of procedure information includes injection information pertaining to injection of at least one of a contrast medium and a diluent into a patient.

35. The interface device of claim 34 wherein said second device is a scanning device and the second set of procedure information includes imaging study information obtained therefrom that is associated with the injection information obtained from said contrast medium injector.

36. The interface device of claim 32 further including a communications link, said communications link for establishing at least one of:
(a) a transmission to a central computer for use thereby of one or more of the records stored in said database;

(b) a reception from said central computer of information affecting operation of said interface device for use thereby;

(c) a transmission to said central computer of operational information pertaining to said interface device at least one of before, during, and after each use thereof;

(d) a reception of updated software for said interface device from at least one of said central computer and a vendor of said interface device;

(e) a reception of information from a vendor of at least one of said first device, said second device and said information system for use thereby;

(f) a transmission to said central computer of statistical information about operation of at least one of said first device and said second device received therefrom, the statistical information including at least one of usage rate, patterns of use, service history and reliability history of at least one of said first device and said second device;

(g) a transmission to said central computer of operational information received from at least one of said first device and said second device; and (h) a transmission to at least one of said information system and a vendor of said first device of information about equipment used by said first device, the equipment information including data pertaining to use of disposables by said first device.

37. The interface device of claim 32 further including an algorithm for processing the records stored in the database so as to determine therefrom result-oriented information based thereon for communication to at least a central computer.

38. The interface device of claim 32 wherein said information system is a hospital information system.

39. A method of collecting information relating to procedures, the method comprising the steps of:

(a) enabling communication with a first device and a second device;

(b) receiving at least one of before, during and after performance of each of the procedures a set of personal identification information from at least one of said first device, said second device and at least one other device;

(c) receiving automatically at least one of during and after performance of each of the procedures a first set of procedure information from said first device;

(d) receiving automatically at least one of during and after performance of each of the procedures a second set of procedure information from said second device, the second set of procedure information corresponding to the first set of procedure information obtained from the first device;

(e) matching automatically the first set of procedure information with the second set of procedure information related thereto for each of the procedures; and (f) storing automatically as a record in a database the set of patient identification information and the first and the second sets of procedure information related thereto for each of the procedures.

40. The method of claim 39 wherein:

(a) said first device is a contrast medium injector and the first set of procedure information includes injection information pertaining to injection of at least one of a contrast medium and a diluent into a patient;

(b) said second device is a scanning device and the second set of procedure information includes imaging study information obtained therefrom pertaining to at least one image of the patient that is associated with the injection information obtained from said contrast medium injector; and (c) an interface device enables the communication with said contrast medium injector and said scanning device and the receipt of the personal identification information, the injection information and the imaging study information therefrom.

41. The method of claim 39 further including the step of providing a communications link, wherein said communications link is configured to establish at least one of:

(a) a transmission to a central computer for use thereby of one or more of the records stored in said database;

(b) a transmission to said central computer of statistical information about operation of at least one of said first device and said second device received therefrom, the statistical information including at least one of a usage rate, a pattern of use, a service history and a reliability history of at least one of said first device and said second device;

(c) a transmission to said central computer of operational information received from at least one of said first device and said second device; and (d) a transmission to at least one of an information system and a vendor of said first device of equipment information about equipment used by said first device, the equipment information including data pertaining to use of disposables by said first device.

42. The method of claim 41 wherein said communications link is implemented at least in part through at least one of (a) a network, (b) a wired connection and (c) a wireless connection.

43. The method of claim 39 further including the steps of:

(a) providing a communications link; and (b) using an algorithm for processing at least some of the records in the database so as to determine therefrom result-oriented information based thereon for communication to a central computer for use thereby.

* * * * *